(12) United States Patent
Duschl et al.

(10) Patent No.: US 9,476,024 B2
(45) Date of Patent: Oct. 25, 2016

(54) THERMORESPONSIVE SUBSTRATE WITH MICROGELS, METHOD FOR ITS PREPARATION AND CULTURE METHOD FOR BIOLOGICAL CELLS

(75) Inventors: Claus Duschl, Berlin (DE); Andreas Lankenau, Rotkreuz (CH); Stephan Schmidt, Potsdam (DE); Thomas Hellweg, Bielefeld (DE); Erik Wischerhoff, Potsdam (DE); Andre Laschewsky, Potsdam (DE); Jean-Francois Lutz, Kehl (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 263 days.

(21) Appl. No.: 13/634,577

(22) PCT Filed: Mar. 21, 2011

(86) PCT No.: PCT/EP2011/001394
§ 371 (c)(1),
(2), (4) Date: Sep. 13, 2012

(87) PCT Pub. No.: WO2011/116922
PCT Pub. Date: Sep. 29, 2011

(65) Prior Publication Data
US 2013/0005039 A1   Jan. 3, 2013

(30) Foreign Application Priority Data
Mar. 22, 2010   (DE) ........................ 10 2010 012 252

(51) Int. Cl.
| | | |
|---|---|---|
| *C12N 9/00* | (2006.01) | |
| *C12N 5/00* | (2006.01) | |
| *C12M 1/00* | (2006.01) | |
| *C12M 1/12* | (2006.01) | |

(52) U.S. Cl.
CPC ............ *C12N 5/0068* (2013.01); *C12M 23/20* (2013.01); *C12M 25/06* (2013.01); *C12M 25/14* (2013.01); *C12N 2539/10* (2013.01)

(58) Field of Classification Search
CPC .............. C12N 5/0068; C12N 5/0075; C12N 2539/10; C12N 2439/10; C12M 23/20; C12M 25/06; C12M 25/14
See application file for complete search history.

(56) References Cited

U.S. PATENT DOCUMENTS

| | | | |
|---|---|---|---|
| 2002/0071843 A1* | 6/2002 | Li et al. ................. | 424/155.1 |
| 2005/0008828 A1* | 1/2005 | Libera et al. ............ | 428/195.1 |
| 2009/0247666 A1 | 10/2009 | Yu et al. | |

FOREIGN PATENT DOCUMENTS

| | | |
|---|---|---|
| EP | 1312669 A1 | 5/2003 |
| JP | 2008220320 A | 9/2008 |
| JP | 2010057439 A | 3/2010 |
| WO | 2004011669 A2 | 2/2004 |

OTHER PUBLICATIONS

Yoshiyuki et al. Tissue Engineering (2003) 9(5); 1005-1012.*
Fernandez-Barbero et al. Physical Rev. E (2002) 66, 051803 pp. 1-10.*
Hopkins et al. Soft Matter (2009) 5: 4928-4937.*
Kushida et al. Eur. Cell Materials (2005) 10: 23-30.*
von Recum et al. Tissue Engineering (1999) 5(3): 251-265.*
Kushida et al. J. Biomed. Mater. Res. (1999) 45: 355-362.*
Chen et al. J. Biomed. Materials (1998) 42(1): 38-44.*
Andersson et al., "Structural Studies of Poly(N-isopropylacrylamide) Microgels: Effect of SDS Surfactant Concentration in the Microgel Synthesis," J. Polymer Sci. B 44, pp. 3305-3314 (2006).
Boyko et al., "Thermo-Sensitive Poly(N-vinylcapro-lactum-co-acetoacetocyethyl methacrylate) Microgels: 1—Synthesis and Characterization," Polymer, vol. 44, No. 26, pp. 7821-7827, Elsevier, (2003).
Chen et al., "Geometric Control of Cell Life and Death," Science, vol. 276, pp. 1425-1428 (1997).
Cole et al., "Stimuli-Responsive Interfaces and Aystems for the Control of Protein-Surface and Cell-Surface Inter-Actions," Biomaterials, vol. 30, No. 9, pp. 1827-1850, Elsevier, (2009).
De Oliveira et al., "Hydrogels from Polysaccharides. I. Cellulose Beads for Chromatographic Support," Glass Science and Technology, Journal of Applied Polymer Science, vol. 60, No. 1, pp. 63-73, Wiley, (1996).
De Oliveira et al., "Hydrogels from Polysaccharides. II. Beads with Cellulose Derivatives," Journal of Applied Polymer Science, vol. 61, pp. 81-86, Wiley, (1996).
Du et al., "Surface-Directed Assembly of Cell-Laden Microgels," Biotechnology and Bioengineering, vol. 105, No. 3, pp. 655-662 (2010).
Dusseiller et al., "Microfabricated Three-Dimensional Environments for Single Cell Studies", Biointerphases, vol. 1, pp. P1-P4, American Vacuum Society, (2006).
Ebara et al. "The Effect of Extensible PEG Tethers on Shielding Between Grafted Theremo-Responsive Polymer Chains and Integrin-RGD Binding," Biomaterials, vol. 29, No. 27, pp. 3650-3655, Elsevier, (2008).
Engler et al., "Matrix Elasticity Directs Stem Cell Lineage Specification," Cell, vol. 126, pp. 677-689, Elsevier, (2006).

(Continued)

*Primary Examiner* — Susan Hanley
(74) *Attorney, Agent, or Firm* — Caesar Rivise, PC

(57) ABSTRACT

The invention relates to a culture substrate having thermoresponsive microgel particles that have a thermoresponsive polymer and modulator particles fixed to the carrier area of the substrate. The modulator can be a substance that has an adhesion capability with biological cells or a substance that causes cellular reactions that are inducible to binding to surface receptors of biological cells. Methods for preparation and use in culturing cells are given.

19 Claims, 14 Drawing Sheets
(1 of 14 Drawing Sheet(s) Filed in Color)

(56) References Cited

OTHER PUBLICATIONS

Ernst et al., "Control of Cell Detachment in a Microfluidic Device Using a Thermo-Responsive Copolymer on a Gold Substrate," Lab Chip, vol. 7, No. 10, pp. 1322-1329, Fraunhofer Institute for Biomedical Engineering, (2007) (Abstract Only).
Fulda et al., "Monolayer Characteristics of Monodisperse Core-Shell Latex Particles Prepared by Soap Free Emulsion Copolymerization," Progr. Colloid Polym. Sci., vol. 101, pp. 178-183, Steinkopff Verlag, (1996).
Gan et al., "In Situ Gelation of P(NIPAM-HEMA) Microgel Dispersion and its Applications as Injectable 3D Cell Scaffold," Biomacromulecules, vol. 10, No. 6, pp. 1410-1415, American Chemical Society, (2009).
Gao et al., "Structural Control in ATRP Synthesis of Star Polymers Using the Arm-First Method," Macromolecules, vol. 39, pp. 3154-3160, American Chemical Society, (2006).
Hersel et al., "RGD Modified Polymers: Biomaterials for Stimulated Cell Adhesion and Beyond," Biomaterials, vol. 24, No. 24, pp. 4385-4415, Elsevier, (2003).
Hong et al., "Layer-by-Layer Deposited Multilayer Assemblies of Polyelectrolytes and Proteins: From Ultrathin Films to Protein Arrays," Progr. Colloid Polym. Sci., vol. 93, pp. 98-102, American Chemical Society, (1993).
Jia et al., "Hyaluronic Acid-Based Microgels and Microgel Networks for Vocal Fold Regeneration," Biomacromolecules, vol. 7, p. 3336-3344, American Chemical Society, (2006).
Joos et al., "Investigation of Cell Adhesion to Structured Surfaces Using Total Internal Reflection Fluorescence and Confocal Laser Scanning Microscopy," Eur. J. Cell Bio, vol. 85 pp. 225-228, Elsevier, (2006).
Kim et al., "Formation of Thermoresponsive Poly(N-isopropylacrylamide)/Dextran Particles by Atom Transfer Radical Polymerization," Macromol. Rapid Commun., vol. 24, No. 8, pp. 517-521, Wiley-VCH, (2003).
Kim et al., "Swelling Induced Detachment of Chondrocytes Using RGD-Modified Poly(N-isopropylacryl-amide) Hydrogel Beads," Biotechnol. Prog., vol. 18, No. 3, pp. 495-500, American Chemical Society, (2002).
Lynch et al., "Novel Method to Prepare Morphologically Rich Polymeric Surfaces for Biomedical Applications via Phase Separation and Arrest of Microgel Particles," J. Phys. Chem. B., vol. 110, No. 30, pp. 14581-14589, American Chemical Society, (2006).
Lyon et al., "Thermoresponsive Microgel-Based Materials", Chem. Soc. Rev., vol. 38, pp. 865-874, The Royal Society of Chemistry, (2009).
Nagase et al., "Temperature-Responsive Intelligent Interfaces for Biomolecular Separation and Cell Sheet Engineering", J.R. Soc. Interface, vol. 6, pp. S293-S309, The Royal Society, (2009).
Oezyuerek et al., "Sulfated Glyco-Block Copolymers with Specific Receptor and Growth Factor Binding to Support Cell Adhesion and Proliferation", Biomaterials, vol. 30, pp. 1026-1035, Elsevier, (2009).
Pich et al., "Temperature-Sensitive Hybrid Microgels with Magnetic Properties,"Langmuir, vol. 20, pp. 10706-10711, American Chemical Society, (2004).
Retama et al., "Biosensors Based on Acrylic Microgels—A Comparative Study of Immobilized Glucose Oxidase and Tyrosinase," Biosensors and Bioelectronics, vol. 20, pp. 2268-2275, Elsevier, (2005).
Retama et al., "Microstuctural Modifications Induced by the Entrapped Glucose Oxidase in Cross-Linked Polyacrylamide Microgels used as Glucose Sensors," Biomaterials; vol. 24, pp. 2965-2973, Elsevier, (2003).
Saunders et al., "Microgels: From Responsive Polymer Colloids to Biomaterials," Advances in Colloid and Interface Science, vol. 147-148, pp. 251-262, Elsevier, (2009).
Scadden, "The Stem-Cell Niche as an Entity of Action," Nature, vol. 441, pp. 1075-1079, Wiley-VCH, (2006).
Schmidt et al., "Adhesion and Mechanical Properties of PNIPAM Microgel Films and Their Potential Use as Switchable Cell Culture Substrates," Adv. Funct. Mater., vol. 20, pp. 3235-3243 (2010).
Schmidt et al., "Packing Density Control in P(NIPAM-co-Aac) Microgel Monolayers: Effect of Surface Charge, pH, and Preparation Technique," Langmuir, vol. 24, pp. 12595-12602, American Chemical Society, (2008).
Schmidt et al., "Thermoresponsive surfaces by spin-coating of PNIPAM-co-PAA microgels: A Combined AFM and Ellipso-metry Study", Polymer, vol. 49, pp. 749-756, Elsevier, (2008).
Serpe et al., "Doxorubicin Uptake and Relese from Microgel Thin Films," Biomacromolecules, vol. 6, pp. 408-413, American Chemical Society, (2005).
Singh et al., "Covalent Tethering of Functional Microgel Films onto Poly(ethylene terephthalate) Surfaces," Biomacromolecules, vol. 8, pp. 3271-3275, American Chemical Society, (2007).
Spinke et al., "Molecular Recognition at Self-Assembled Monolayers: Optimization of Surface Functionalization," J. Chem. Phys, vol. 99, No. 9, pp. 7012-7019, American Institute of Physics, (1993).
Stile et al., "Thermo-Responsive Peptide-Modified Hydrogels for Tissue Regeneration," Biomacromolecules, vol. 2, pp. 185-194, American Chemical Society, (2001).
Von Recum et al., "Novel Thermally Reversible Hydrogel as Detachable Cell Culture Substrate," Journal of Biomedical Materials Research, vol. 40, pp. 631-639, Wiley, (1998).
Williams et al., "Aligned Cell Sheets Grown on Thermo-Responsive Substrates with Microcontact Printed Protein Patterns", Adv. Mater., vol. 21 pp. 2161-2164, Wiley-VCH, (2009).
Wischerhoff et al., "Controlled Cell Adhesion on PEG-Based Switchable Surfaces," vol. 47, pp. 5666-5668, Wiley-VCH, (2008).
Wu et al., "The Kinetics of Poly(N-isopropylacrylamide) Microgel Latex Formation," Coll. Poly. Sci., vol. 272, pp. 467-477 (1994).
Yamada et al., "Thermo-Responsive Polymeric Surfaces; Control of Attachment and Detachment of Cultured Cells," Makromol. Chem., Rapid Commun., vol. 11, pp. 571-576, Huthig & Wepf, (1990).
Zhang et al., "Preparation of AgCl-polyacrylamide Composite Microspheres via Combination of a Polymer Microgel Template Method and a Reverse Micelle Technique," Journal of Colloid and Interface Science, vol. 300, pp. 210-218, Elsevier, (2006).
Zhao et al., "Electrochemical Biosensors Based on Layer-by-Layer Assemblies", Electroanalysis, vol. 18, pp. 1737-1748, Wiley-VCH, (2006).
Zhu et al., "The Synthesis and Characterization of Polymerizable and Biocompatible N-Maleic Acyl-Chitosan," Journal of Biomedical Materials Research Part B: Applied Biomaterials, vol. 85B, No. 2, pp. 489-495, Wiley, (2008).
International Search Report for PCT/EP2011/001394 dated Jan. 24, 2012.
Schuller, "Kolloidphysikalische Untersuchungen an Kunststoff-Latices", Kolloid Z.Z. Polym., vol. 211, pp. 113-121 (1966).

\* cited by examiner

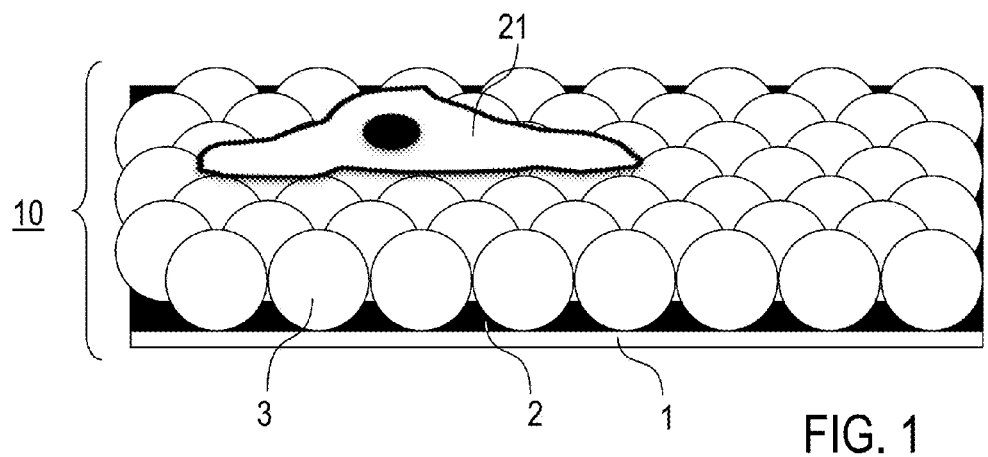
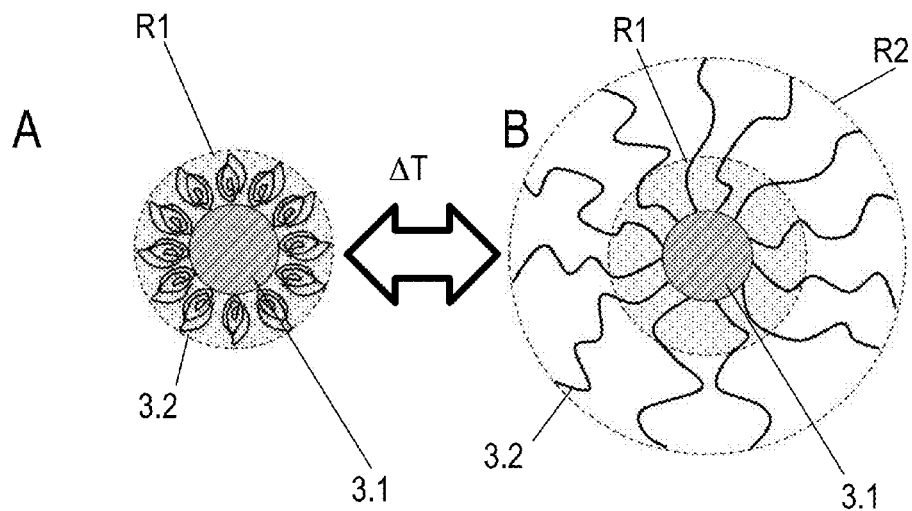
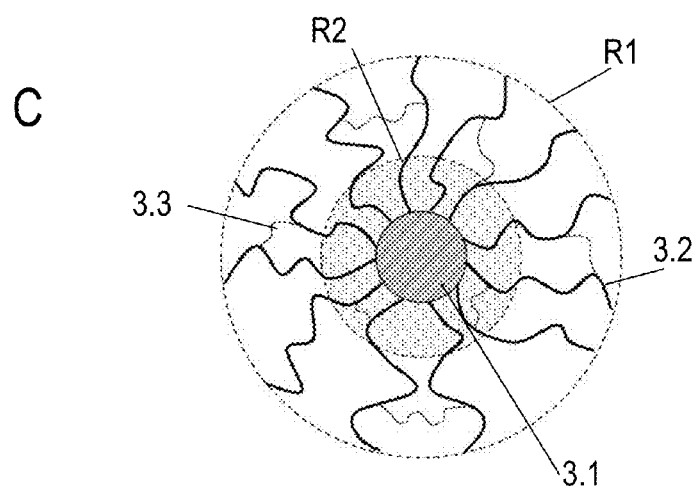
FIG. 1
FIG. 2

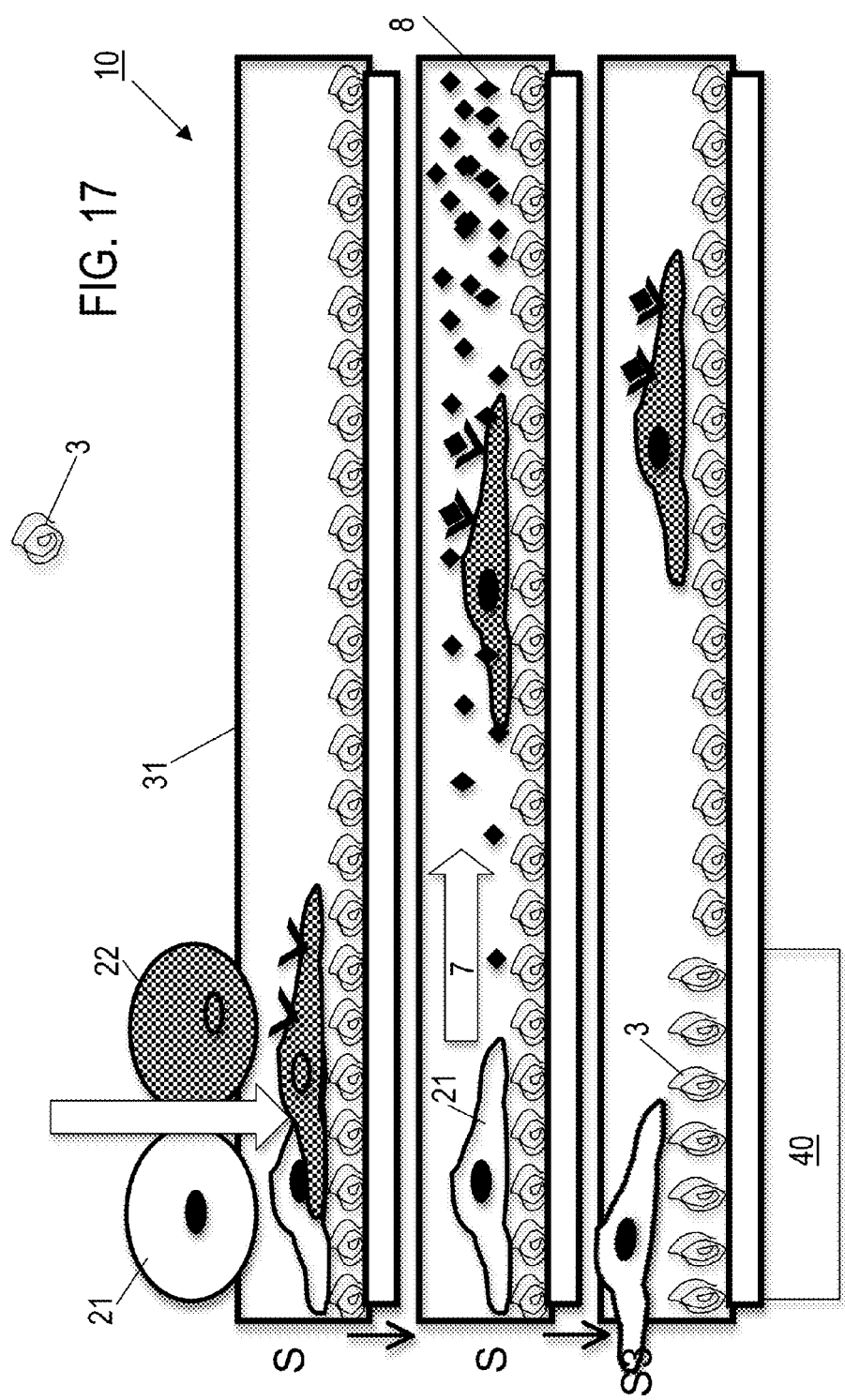

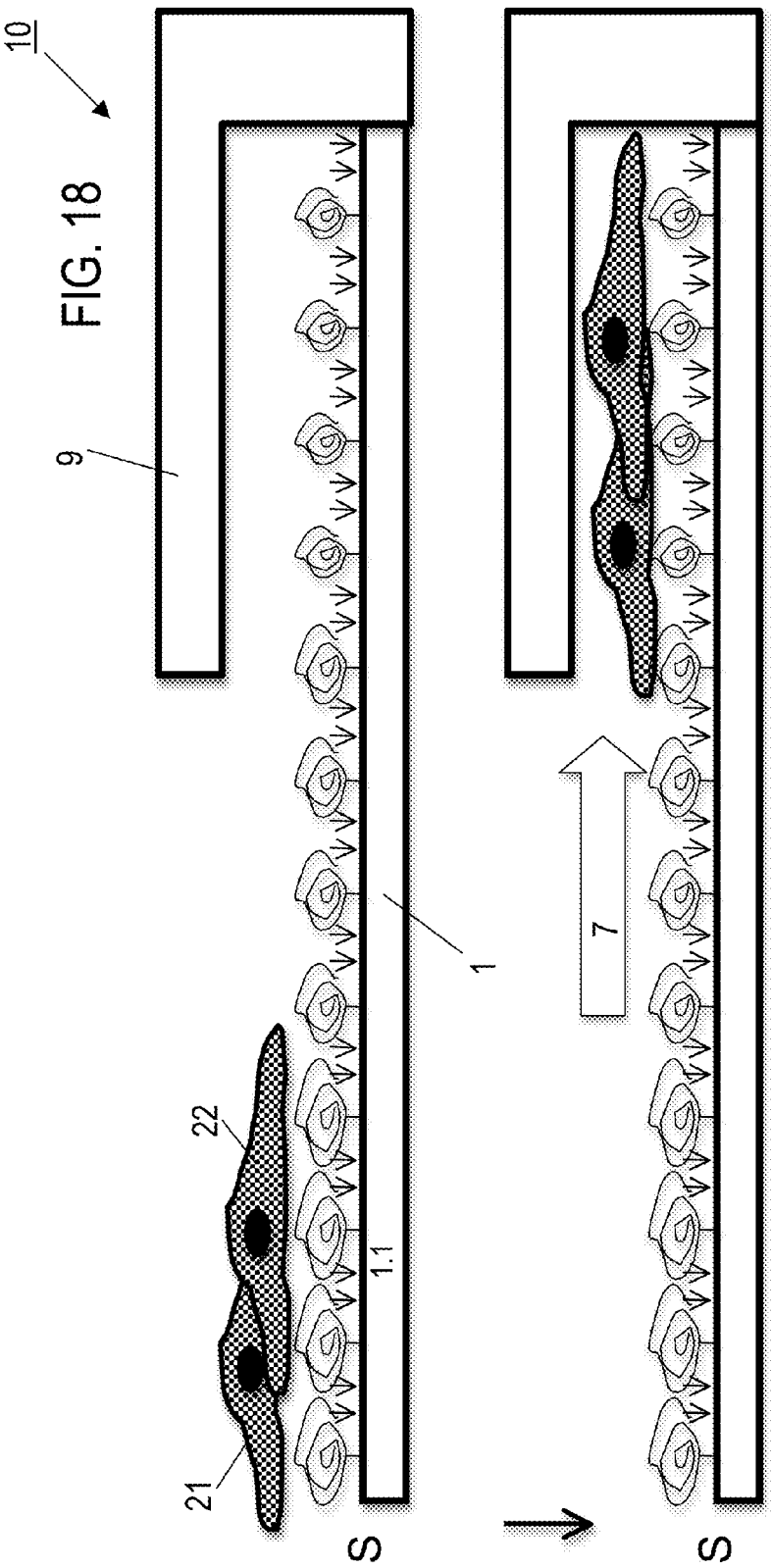

THERMORESPONSIVE SUBSTRATE WITH MICROGELS, METHOD FOR ITS PREPARATION AND CULTURE METHOD FOR BIOLOGICAL CELLS

BACKGROUND OF THE INVENTION

The invention relates to a thermoresponsive substrate for receiving biological cells, in particular a substrate whose surface properties are variable as a function of the temperature. Furthermore, the invention relates to a method for the preparation of such a substrate, in particular a method for the application of thermoresponsive polymer material to a substrate body. Furthermore, the invention relates to a method for the cultivation of biological cells on a thermoresponsive substrate. Applications of the invention are given in the in vitro cultivation of biological cells.

It is generally known to cultivate living biological cells on substrates external to an organism (in vitro cultivation). A substrate intended for cultivation (cultivation substrate) typically features a solid substrate body, e.g. made of glass or plastic, whose surface (carrier area) is functionalized. By means of the functionalization, comprising, for example, a plasma treatment, a coating with proteins (such as e.g. fibronectin, collagen) or a coating with polymers (such as e.g. polylysine), an interaction of the cells with the surface is influenced. There is interest in cultivation substrates allowing for targeted manipulation of the biological cells and in particular influencing of, for example, the adhesion, migration, proliferation, differentiation or cell transformation (formation of tumor cells). The gentle detachment of the cells from the surfaces in particular is a fundamental problem. This occurs typically via an enzyme treatment (trypsination) which can lead to damages to and losses of the cells.

It was found in experiments that properties of biological cells can be influenced through the hardness of the surface of the cultivation substrate. Hardness variations obtained by sequential coatings with polyacrylamide and biomolecules, for example, led to different differentiations of mesenchymal stem cells (see Discher et al. in "Cell" 126 (2006), 677-689). Furthermore, it is known that the adhesion of biological cells depends on the hardness of the substrate surface.

Furthermore, thermoresponsive polymers are known. A thermoresponsive polymer is characterized by having a switching temperature ("lower critical solution temperature" (LCST)) in aqueous media. Aqueous media are e.g. pure water, commercially available buffer solutions, cell culture media or mixtures of water with organic solvents. Below the switching temperature, aqueous solutions of thermoresponsive polymers are monophasic, above this temperature biphasic. When thermoresponsive polymers are immobilized on surfaces, they perform a phase transition (conformational transition) in aqueous media when the switching temperature is exceeded; they are more strongly hydrated below the switching temperature than above.

It was found that the adhesion on substrates which are coated with the thermoresponsive (thermosensitive) polymer poly-(N-isopropyl acrylamide) ("PNIPam") or derivatives thereof and feature the temperature-dependent hydration can be influenced in a targeted manner as a function of the temperature (see N. Yamada et al. in "Makromol. Chem." 11 (1990), 571; C. Williams et al. in "Adv. Mater." 21 (2009), 2161-2164, O. Ernst et al. in "Lab Chip" 7 (2007), 1322). This property was also shown with polyethylene glycol (PEG)-based polymers (see E. Wischerhoff et al. in "Angew. Chem." (2008), 5666).

Conventional substrates whose surfaces are coated with thermoresponsive polymers (e.g. WO 2004/011669) can have disadvantages both in terms of the preparation of the coating and the suitability for cell cultivation. For example, the preparation of a substrate coated with a thermoresponsive polymer requires several elaborate process steps which are realized with an expensive apparatus assembly. Furthermore, there is only limited variability of the polymer composition. For example, the thermal response behavior of the thermoresponsive polymer can change or disappear if a second polymer component is added to the polymer. Thus, there is only limited flexibility with regard to the introduction of another functionalization of a substrate coated with a thermoresponsive polymer.

Different protocols for the functionalization of the substrate body were developed for the preparation of substrates coated with thermoresponsive polymers, such as e.g. reactions with silanes, a plasma treatment or a chemical treatment. In this connection, functional groups, such as e.g. $-NH_2$, $-COOH$ or epoxides, are provided on the surface of the substrate body which enable the complementary functionalized molecules, such as, in particular, the thermoresponsive polymers, a covalent attachment. In this connection, a limited reproducibility and controllability of the functionalization, in particular with regard to the attachment density and homogeneity, as well as the limitation to specific substrate materials and chemical substances and a limitation to hard, planar substrate bodies have proven to be disadvantageous. The preparation of a surface with defined mixtures of different molecules is only possible in specific exceptional cases and with a great deal of effort.

The following property of thermoresponsive polymers has particularly proven to be disadvantageous for the cultivation of biological cells. A thermoresponsive polymer is in general a polymer which experiences a physical phase transition as a function of the temperature, wherein a rearrangement of polymer chains takes place, for example. While the phase transition in a liquid solution within a temperature range of a few ° C. is sharply defined, thermoresponsive polymers immobilized in layers are characterized by a wide temperature profile of the phase transition. Thus, it was found that a cooling-down from 37° C. to temperatures below 20° C. for up to an hour is required for certain types of adherent cells to release the adhesion from the surface of the substrate (see "Application Notes" for the PNIPam-coated UpCell cultivation substrates from the manufacturer Nunc). However, such a cooling-down for this time is undesired due to the possible influencing of the cell function associated therewith. Furthermore, it was discovered in practice that thermoresponsive polymer layers can be insufficiently effective for different cell lines, such as e.g. MCF7 tumor cells or MG63 osteoblast cells.

Conventional techniques are further characterized by disadvantages in the cultivation with so-called co-cultures. As a cell type to be cultivated requires messengers (paracrine factors) from other cells for the growth or the maintenance of vitality in the adherent state, the cultivation, the growth or manipulative or analytical processes of adherent cells often have to be performed together in the co-culture (e.g. stem cells and feeder cells or melanocytes and keratinocytes). For the subsequent separation of the cells, only methods based on a cell separation in liquid cell suspensions are available up to now. For this, the cells have to be detached from the substrate and transferred into a separating device (flow cytometer) which has significant disadvantages due to the time and preparation expenditure and the low yield. In particular for samples with cell counts of less than $10^5$ cells, the conventional cell separation is not workable as an excessively high number of cells is lost during the formation of the suspension and the separation in the flow cytometer.

OBJECTS OF THE INVENTION

The object of the invention is to provide an improved thermoresponsive substrate for receiving biological cells, by means of which disadvantages of the conventional technique are overcome. The object of the invention is in particular to provide an improved thermoresponsive substrate which is characterized by simple preparation, high flexibility in the setting of surface properties, expanded functionalization capability, suitability for an increased number of cell types and/or suitability for a gentle cell cultivation and adhesion control with small temperature differences. Another object of the invention is to provide an improved method for the preparation of a thermoresponsive substrate, in particular for receiving biological cells, by means of which disadvantages of conventional methods for the substrate preparation are overcome. Another object of the invention is to provide an improved culture method using a thermoresponsive substrate, by means of which disadvantages and limitations of conventional culture methods are overcome.

These objects are achieved by a substrate and a method of the invention.

SUMMARY OF THE INVENTION

According to a first aspect of the invention, a substrate, in particular for receiving biological cells, is provided which has a substrate body having a carrier area. According to the invention, thermoresponsive microgels are disposed on the carrier area. In contrast to conventional thermoresponsive substrates having isotropic or homogeneous polymer layers, the substrate according to the invention is characterized by a carrier area of the substrate body on which thermoresponsive microgels (particles containing a thermoresponsive or thermosensitive polymer) are exposed. The thermoresponsive microgels are polymer particles fixed to the carrier area which exhibit a physical phase transition between different hydration states at a predetermined critical temperature (switching temperature).

According to a second aspect of the invention, a method for the preparation of the substrate according to the invention is provided wherein thermoresponsive microgels are produced as a dispersion (microgel dispersion, µ-gel dispersion). To provide the thermoresponsive microgels on the carrier area of the substrate body, the dispersion is applied to the carrier area wherein thermoresponsive microgels which contact the carrier area are connected with the latter while excessive microgels are separated, e.g. washed off the carrier area.

According to a third aspect of the invention, a method for the cultivation of biological cells on the substrate according to the invention is provided wherein the biological cells are disposed in contact with the exposed thermoresponsive microgels. According to the invention, cultivation conditions for the cells on the substrate are set such that the cells are subjected to a nondestructive detachment (separation from the substrate), a growth, a differentiation and/or a cell migration.

The provision of a cultivation substrate having thermoresponsive microgels according to the invention has a number of advantages with regard to the setting of physical and/or chemical surface properties, the targeted modification of surface properties, the preparation of the substrate and the creation of new applications or functions of cultivation substrates. The inventors have found that the phase transition of the thermoresponsive microgels takes place within a narrow temperature range which is comparable with the narrow temperature profile of the phase transition of dissolved thermoresponsive polymers. Wide temperature profiles over intervals of 20° C. to 30° C., as they occur with conventional, isotropic polymer layers, are avoided according to the invention.

The inventors have found that the phase transition is characterized by a change of the solidity parameter of the thermoresponsive polymer (e.g. hardness, plastic or elastic deformability, in particular Young's modulus). Together with the solidity parameter, the adhesion of cells changes below and above a critical temperature of the phase transition (switching temperature of the polymer). At the same time, the water content of the thermoresponsive polymer changes. As a result, the adhesion of the cells is influenced. The setting of the adhesion is advantageously possible with higher reliability and reproducibility than with conventional polymer layers. The inventors have found that with the phase transition of the immobilized microgels, a significantly increased number of surface interactions is offered or interrupted and thus the reliability of a temperature-controlled release of the cells is improved.

With regard to the targeted modification of surface properties, it has shown to be particularly advantageous that substrates according to the invention can be subjected to a functionalization for the biological cells without the thermoresponsive microgels losing their response behavior. Advantages for the preparation of the substrate according to the invention result from the stability of the particle dispersion over weeks or months and the immediate usability of the substrate after the coating of the carrier area with the microgels. The functionalization of thermoresponsive substrates provides new applications, e.g. for a passive control of a cell migration on the substrate surface or a targeted detachment of cells in predetermined substrate regions.

The substrate according to the invention is a cultivation substrate for biological cells. The substrate is configured for receiving biological cells and providing physiological cultivation conditions. In particular, the substrate is adapted for receiving the cells in a liquid cultivation medium, i.e. the carrier area is suited to receive the cultivation medium. The substrate body may be produced from a solid material which can be stiff or resilient (ductile). The material of the substrate body is preferably temperature-stable and in particular not thermoresponsive. The carrier area is preferably a flat area, however, alternatively, it can be formed such that it is curved.

The thermoresponsive microgels include a polymer which exhibits the phase transition in a physiological temperature range. The phase transition which is in particular a volume phase transition preferably takes place at a temperature below 40° C., in particular below 37° C., e.g. below 35° C. The phase transition preferably takes place at a temperature above 10° C., in particular above 20° C., e.g. above 32° C. The temperature interval wherein the phase transition takes place is preferably smaller than 15° C., in particular smaller than 20° C., such as e.g. 5° C. or less.

The thermoresponsive microgels are preferably made from at least one uncharged and non-ionizable polymer. With particular preference, the microgels consist at least on their surface of the at least one uncharged and non-ionizable polymer. By doing so, undesired interactions with the cell surface are advantageously minimized.

According to preferred embodiments of the invention, the thermoresponsive microgels are formed from at least one of the polymers of the following polymers or polymer groups:

(1) poly-(N-isopropyl acrylamide), (2) $-X-(-CH_2-CR_1COO-R_2-)_n-(-CH_2-CR_1COO-R_3-)_m-R_4$ or a copolymer thereof, (3) $-X-[(-CH_2-CR_1COO-R_2-)_n-(-CH_2-CR_1COO-R_3-)_m-R_4]_2$ or a copolymer thereof, wherein X is a coupling group to the carrier area, $R_1$=H or $CH_3$, $R_2/R_3$=aliphatic hydrocarbon chains having at least one ether group, preferably having 1 to 20 ether groups (preferably polyethylene oxide), and $R_4$ is —H, an aliphatic hydrocarbon chain or a functional group, such as e.g. -halogen, $-N_3$, -thiocarbonyl, -(di)thiocarbamyl (4) homo- or copolymers of the general structure

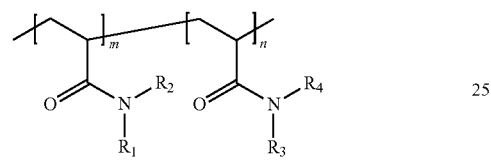

with $R_1$, $R_2$, $R_3$ and $R_4$=H or alkyl, preferably $R_1$ isopropyl, $R_2$=H, n=0, (5) homo- or copolymers of the general structure

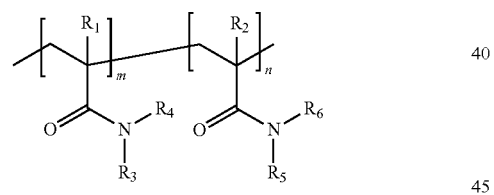

with $R_1$, $R_2$=—H, -alkyl, preferably —H and —$CH_3$, particularly preferably —H with $R_3$, $R_4$, $R_5$ and $R_6$=—H, -alkyl, alkenyl, alkynyl, aryl, preferably —$R_3$=-isopropyl, —$R_4$=—H, —$R_5$ and —$R_6$=—$C_2H_5$, —$CH_3$ or —H, particularly preferably —$R_3$=-isopropyl and —$R_4$=—H and m:n=100:0 and/or $R_3$, $R_4$, $R_5$ and

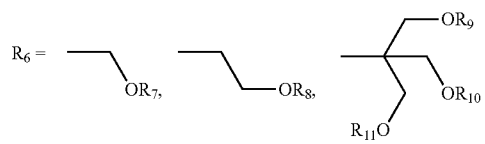

with $R_7$ to $R_{11}$=—H, -alkyl, alkenyl, alkynyl, aryl, -alkyloyl, at least one R=H, (6) homo- or copolymers of the general structure

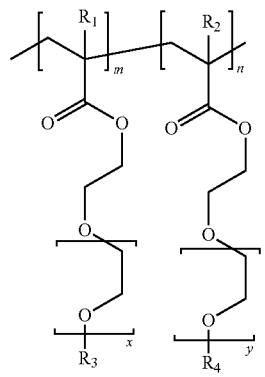

with $R_1$, $R_2$=H or $CH_3$, $R_3$, $R_4$=H or alkyl, x, y=0 to 20, (7) homo- and copolymers of the general structure

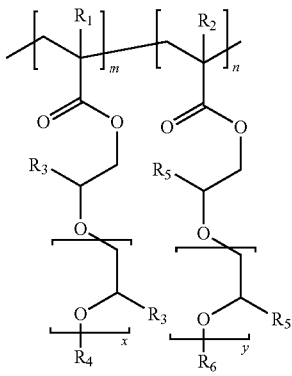

with $R_1$, $R_2$=—H, -alkyl, preferably —H and —$CH_3$, particularly preferably —$CH_3$, with $R_3$, $R_5$=—H, -alkyl, alkenyl, alkynyl, aryl, preferably —H and —$CH_3$, particularly preferably —H, wherein:

if $R_3 \neq$—H, $R_5$=—H with $R_4$, $R_6$=—H, -alkyl, alkenyl, alkynyl, aryl, preferably —H and/or —$CH_3$, particularly preferably —$CH_3$, wherein if $R_3$, $R_5$=—H and $R_4$, $R_6$=—$CH_3$, x=1 and y=7.5, m:n is preferably between 95:5 and 90:10, particularly preferably at 93:7, and if $R_3$, $R_5$=—H and $R_4$, $R_6$=—$CH_3$, x=1 and y=4.5, m:n is preferably between 93:7 and 80:20 and particularly preferably at 85:15, (8) homo- and copolymers of the general structure

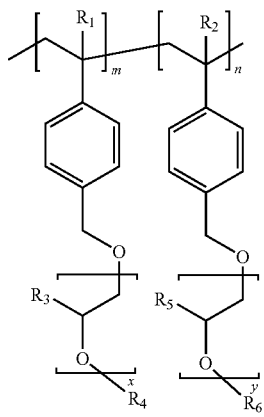

with $R_1$, $R_2$=—H, -alkyl, preferably —H and —CH$_3$, particularly preferably —H,
with $R_3$, $R_5$=—H, -alkyl, alkenyl, alkynyl, aryl, preferably —H and —CH$_3$, particularly preferably —H, wherein if $R_3 \neq$—H, $R_5$=—H
with $R_4$, $R_6$=—H, -alkyl, alkenyl, alkynyl, aryl, preferably —H and/or —CH$_3$, particularly preferably —H, wherein if $R_1$, $R_2$=—H and $R_4$, $R_6$=—H, x=3 and y=4, m:n is preferably between 65:35 and 45:55, particularly preferably between 60:40 and 50:50, (9) homo- and copolymers of the general structure

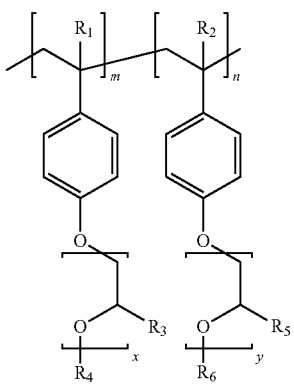

with $R_1$, $R_2$=—H, -alkyl, preferably —H and —CH$_3$, particularly preferably —H,
with $R_3$, $R_5$=—H, -alkyl, alkenyl, alkynyl, aryl, preferably —H and —CH$_3$, particularly preferably —H, wherein if $R_3 \neq$—H, $R_5$=—H,
with $R_4$, $R_6$=—H, -alkyl, alkenyl, alkynyl, aryl, preferably —H and/or —CH$_3$, particularly preferably —H,

(10) homo- or copolymers of the general structure

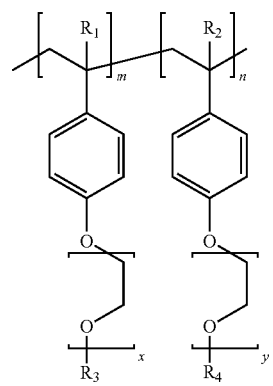

with $R_1$, $R_2$=H or CH$_3$, $R_3$, $R_4$=H or alkyl, x, y=2 to 20,

(11) homo- or copolymers of the general structure

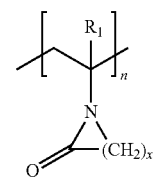

with $R_1$=H or CH$_3$, x=3 to 5, copolymers with x=3 and X>3,

(12) homo- or copolymers of the general structure

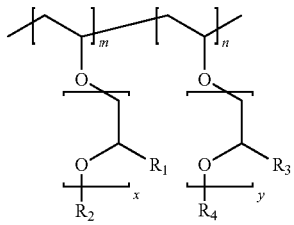

with $R_1$, $R_3$=—H, -alkyl, alkenyl, alkynyl, aryl, preferably —H and —CH$_3$, particularly preferably —H, wherein if $R_3 \neq$—H, $R_5$=—H,
with $R_2$, $R_4$=—H, -alkyl, alkenyl, alkynyl, aryl, preferably —H and/or —CH$_3$, particularly preferably —CH$_3$,

(13) homo- or copolymers of the general structure

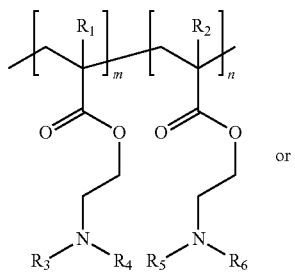

or

-continued

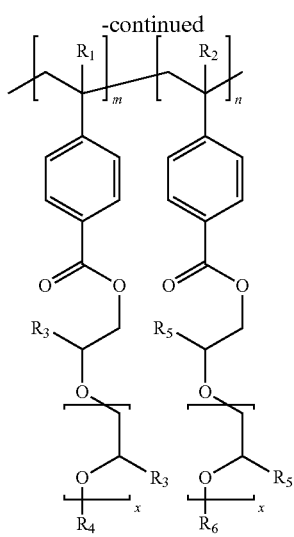

with $R_1$, $R_2$=—H, -alkyl, preferably —H and —CH$_3$, particularly preferably —H, with $R_3$, $R_5$=—H, -alkyl, alkenyl, alkynyl, aryl, preferably —H and —CH$_3$, particularly preferably —H, wherein if $R_3 \neq$—H, $R_5$=—H, with $R_4$, $R_6$=—H, -alkyl, alkenyl, alkynyl, aryl, preferably —H and/or —CH$_3$, particularly preferably —H,

(14) homo- or copolymers of the general structure

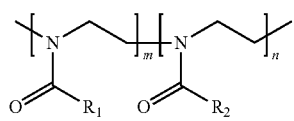

with $R_1$, $R_2$=—H, -alkyl, alkenyl, alkynyl, aryl,

(15) homo- or copolymers of the general structure

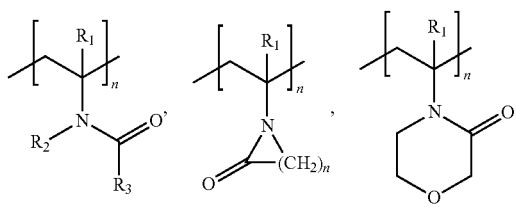

or copolymers of the three elements in compositions with $R_1$=—H, -alkyl, preferably —H and —CH$_3$, particularly preferably —H, with $R_2$, $R_3$=—H, -alkyl, alkenyl, alkynyl, aryl with $2 \leq n \leq 10$, preferably $3 \leq n \leq 6$

(16) homo- or copolymers of the general structure

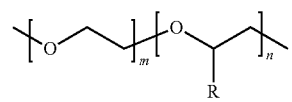

with —R=—H, -alkyl, alkenyl, alkynyl, aryl, preferably —R=-alkyl, particularly preferably —R=—CH$_3$,

(17) homo- or copolymers of the general structure

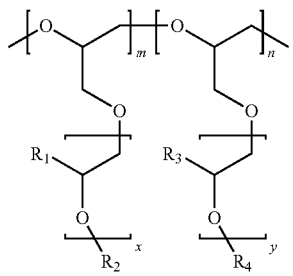

with $R_1$, $R_3$=—H, -alkyl, alkenyl, alkynyl, aryl, preferably —H and —CH$_3$, wherein
if $R_1 \neq$—H, $R_3$=—H
with $R_2$, $R_4$=—H, -alkyl, alkenyl, alkynyl, aryl, preferably —H and/or —CH$_3$,

(18) homo- or copolymers of the general structure

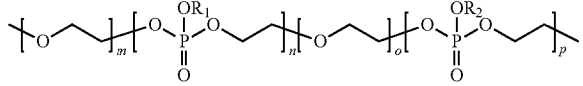

with $R_1$, $R_2$=—H, -alkyl, alkenyl, alkynyl, aryl,

(19) homo- or copolymers of the general structure

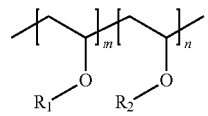

with $R_1$, $R_2$=—H, -alkyl, alkenyl, alkynyl, aryl, preferably $R_1$=—CH$_3$, n=0,

(20) homo- or copolymers of the general structure

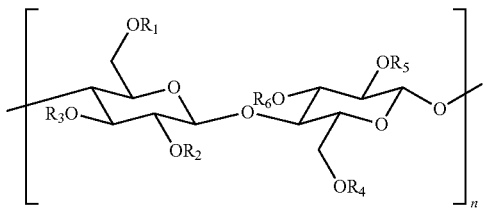

with $R_1$ to $R_6$=—H, -alkyl, alkenyl, alkynyl, aryl, -alkyl-oyl, at least two R=H,

(21) homo- or copolymers of an analogous structure as under 19, based on other polysaccharide scaffolds than cellulose,

(22) homo- or copolymers with elastine-like units,

(23) copolymers of all the above-mentioned units with changed monomers.

The mentioned copolymers can be random, alternating or block copolymers.

In the polymers according to (4) to (25), at least one terminal unit of the polymer backbone preferably includes a coupling group to the carrier area.

The carrier area can be the immediate surface of the substrate body, e.g. made of glass, silicon or plastics, such as polystyrene, COP (cycloolefin polymer), polycarbonate, or can be formed on this by a metal film, e.g. made of gold, silver, platinum, titanium or chromium. Depending on the chemical composition of the carrier area, X can be a functional group, such as e.g. —SS—, —SH, —COOH, —NH$_2$ (SS is a bilaterally, symmetrically substituted disulfide group). Preferably, n+m is >10.

These polymers have proven to be particular advantageous in terms of biocompatibility and flexibility when setting physical or chemical surface properties.

The microgels on the carrier area can all be formed identically from a single polymer. When the microgels are formed from at least two different polymers according to an alternative variant, this can result in advantages in the setting of the surface properties. Furthermore, in this case, microgels having different compositions can be disposed on the carrier area. Microgels having different compositions can be arranged separately according to subregions, for example, to provide different cultivation conditions on the carrier area. Alternatively, the microgels having the different compositions can be disposed admixed and distributed on the carrier area. Alternatively or additionally, the microgels can have different diameters. For example, thermoresponsive microgels having different diameters can be fixed separately in different subregions of the carrier area or be disposed admixed and distributed on the carrier area.

Advantageously, microgels having predetermined diameters of the dispersed, colloidal particles can be produced (see M. Andersson, S. L. Maunu in "J. Poly. Sci." B 44 (2006), 3305; X. Wu et al. in "Coll. Poly. Sci." 272 (1994), 467). This allows to targetedly set the size or, if particles having different diameters are disposed, the different sizes of the thermoresponsive microgels. According to preferred embodiments of the invention, the thermoresponsive microgels have a diameter of at least 10 nm, in particular at least 20 nm, particularly preferably at least 50 nm, such as e.g. at least 100 nm. The upper limit of the particle diameter is preferably 50 µm. The diameter of the thermoresponsive microgels is particularly preferably less than or equal to 30 µm, in particular less than or equal to 20 µm, such as e.g. 10 µm or less, e.g. less than 1 µm.

According to another variant, the thermoresponsive microgels can have a core-shell structure, wherein a core can consist of either a non-thermoresponsive material, in particular a solid carrier particle, or a cross-linked thermoresponsive material. The shell preferably consists exclusively of the thermoresponsive polymer material. The use of the solid carrier particle which can be formed from inorganic glass, metal, ceramics or plastics, in particular polymethyl methacrylate or polystyrene, for example, can have advantages with regard to the provision of a certain minimum hardness of the surface of the substrate according to the invention. The cohesion of the cores of the thermoresponsive microgels is preferably caused by secondary-valence interactions (non-covalent interactions between molecules, such as van der Waals interaction, hydrogen bridge bond, hydrophobic interaction) or by chemical cross-linking.

Furthermore, core-shell particles offer the possibility to integrate non-cross-linked or weakly cross-linked polymer chains into a microgel without affecting the mechanical cohesion of the particle. Non-cross-linked or weakly cross-linked microgels have the advantage that the thermoresponsive chains remain very mobile and the conformational change during the phase change thus can have a better effect. If weakly cross-linked particles are employed, the cross-linking density should be no more than 1 per 20 repeating units and preferably be between 1 per 100 and 1 per 500 repeating units. To achieve a pronounced thermoresponsive effect, the thickness of the shell should be at least 10 nm and at most 400 nm, preferably be between 30 and 100 nm. General examples for the production of core-shell particles are given, for example, by Schuller in "Kolloid Z. Z. Polym." 211, 113-121 (1966), Fulda et al. in "Progr. Colloid Polym. Sci." 101, 178-183 (1996), or Gao et al. in "Macromolecules" 39, 3154-3160 (2006).

The thickness of the layer of thermoresponsive microgels on the carrier area is preferably less than or equal to the diameter of the microgels. The microgels preferably form a monolayer. In particular, a closed monolayer, i.e. a closed covering of the carrier area with the microgels, or a submonolayer with gaps between the microgels can be provided. As the fixed microgels can have a leveled shape, the thickness of the layer of thermoresponsive microgels can be less than the particle diameter. In comparison to multilayers, microgel monolayers have the advantage that the adhesion of the biological cells can be controlled with greater reliability.

Alternatively, a layer can include several layers of the thermoresponsive microgels. In this case, advantages can result due to a greater robustness to defects.

According to a particularly preferred embodiment of the invention, the carrier area can be provided with an adhesion promoter. Every substance that is suitable for the immobilization of the microgels and biocompatible can be used as an adhesion promoter. The adhesion promoter can form a covalent bond with the carrier area and the thermoresponsive polymer, for example. Furthermore, specific biological receptor-ligand bonds, such as e.g. the bond of streptavidin and biotin, can be used for the immobilization of the polymers. Finally, the adhesion promoter can be construed for coupling the polymer by an unspecific interaction, such as e.g. a charge interaction, a hydrophobic interaction or a van der Waals interaction. By means of these interactions, the thermoresponsive polymer is well anchored on the carrier area, regardless of the temperature. The anchoring of the particles on the carrier area persists, regardless of the phase transition of the thermoresponsive polymer.

According to another, particularly preferred embodiment of the invention, the substrate is provided with at least one modulator substance. The at least one modulator substance is disposed on the exposed surface of the substrate, i.e. between the thermoresponsive microgels and/or at least partially covering these. Advantageously, the provision of the at least one modulator substance allows for a functionalization of the substrate. Thus, this embodiment of the invention constitutes a significant improvement in comparison to conventional cultivation substrates having thermoresponsive polymers which would be unsuited for such a functionalization. In contrast thereto, the at least one modulator substance allows for influencing of the cultivation conditions on the substrate without affecting the temperature behavior of the microgels.

Advantageously, different types of modulator substances can be provided alone or in combination. For example, modulator substances can be provided which increase the adhesion capability of the biological cells (adhesion-increasing modulator substances, cell-attracting molecules). In this connection, at least one of the following substances is provided:

biomolecules, such as e.g. fibronectin, collagen, laminin,
      -adhesion-promoting peptides, such as e.g. peptides
        including the amino acid sequence RGD,
    synthetic polymers, such as e.g. poly-L-lysine, polystyrene sulfonate, polyallylamine, polyethyleneimine.

Alternatively, modulator substances can be provided which reduce the adhesion capability of the biological cells (adhesion-reducing modulator substances, cell-repelling molecules). In this case, at least one of the following substances is used as a modulator substance:

proteins, such as e.g. bovine serum albumin, BSA,
adhesion-reducing peptides, such as e.g. peptides with a high leucine and isoleucine content,
synthetic polymers, such as e.g. polymers including chains of polyethylene glycol ("PEG"), and
lipids.

Furthermore, adhesion-increasing and adhesion-reducing modular substances can be provided combined on a substrate. For example, the modulator substances having different effects can be disposed separately in different subregions of the carrier area or be disposed admixed and distributed on the carrier area. In the latter case, an effective adhesion capability can be set in the surface of the substrate via the mixing ratio of adhesion-increasing and adhesion-reducing modulator substances, wherein the temperature-dependent fixing or detachment of cells is maintained via the simultaneous provision of the thermoresponsive microgels.

According to another variant of the invention, a modulator substance can be provided alternatively or additionally which is suitable for inducing cellular reactions in the biological cells. For example, it can be provided for a modulator substance attaching to surface receptors of the cells to trigger the reactions. For this function, substances, such as e.g. proteins of the extracellular matrix (ECM), such as fibronectin, antibodies to receptors (EGFR) binding growth factors, or antibodies e.g. to CD 28 and CD 3 of T-cells (activation of the immune response), are particularly preferably provided.

Another advantage of the invention results from the flexibility of the provision of the at least one modulator substance. According to a first variant, modulator particles are provided which consist of the at least one modulator substance or are coated with it and are disposed between the thermoresponsive microgels on the carrier area. The modulator particles can advantageously be added to the microgel and applied with the latter to the carrier area. Alternatively or additionally, the at least one modulator substance can be formed as a substance layer on the carrier area on which the thermoresponsive particles can be disposed.

According to another embodiment of the invention, a spatial modulation of the surface properties of the substrate on the carrier area can advantageously be provided. The carrier area has different surface properties in at least two subregions. Advantageously, the subregions can be formed by disposing at least one of the thermoresponsive microgels, the adhesion promoter and the at least one modulator substance on the carrier area having at least one spatial density gradient. At least one of the mentioned components of the surface of the substrate is provided with a spatial density which is variable in at least one direction along the carrier area. The density gradient can be formed incrementally or continuously. The provision of the at least one density gradient advantageously allows the cells along the carrier area to present different adhesion capabilities, different temperature reactions, different cellular reactions, such as e.g. different differentiations, and/or different cell migrations.

According to another advantageous embodiment of the invention, at least one cultivation cavity can be provided on the carrier area. The cultivation cavity is a protrusion projecting beyond the carrier area which is formed partially covering the carrier area. The cultivation cavity comprises e.g. the shape of a unilaterally open hollow space or a pocket and is adapted for receiving at least one biological cell. By means of the cultivation cavity, spatial cultivation conditions are replicated which are given in the cultivation in a cell aggregate.

Advantageously, the at least one density gradient for the functionalization of the surface of the substrate can be formed in such a way that cells migrate to the cultivation cavity to be subjected there to another cultivation and/or differentiation.

The substrate according to the invention is construed for the cultivation of biological cells. To this end, the substrate body is preferably a part of a cultivation device, such as e.g. a culture vessel or a fluidic device, in which cells are cultivatable, such as e.g. a fluidic microsystem. The substrate body can be fixed with the cultivation device, e.g. form the bottom of the culture vessel, or can be detachable from the cultivation device, e.g. constitute a part that can be inserted into a culture vessel.

The method according to the invention for the cultivation of biological cells can be performed with one or more of the following method steps. For example, the setting of the adhesion of the biological cells on the substrate can be provided by setting the temperature of the substrate. The setting of the temperature can be provided globally for the entire substrate or locally for at least one subregion. By means of setting the temperature, a solidity parameter of the substrate surface is influenced. Furthermore, the setting of a cell type-specific migration of at least one type of the biological cells can be provided by instigating at least one cell type, e.g. at least one differentiation type, along a density gradient of a modulator substance to migrate. Furthermore, the setting of the migration of at least one cell type can be provided by means of the density gradient of the modulator substance such that the biological cells migrate into a cultivation cavity.

BRIEF DESCRIPTION OF SEVERAL VIEWS OF THE DRAWINGS

The patent or application file contains at least one drawing executed in color. Copies of this patent or patent application publication with color drawing(s) will be provided by the Office upon request and payment of the necessary fee.

Further details and advantages of the invention will be described below with reference to the attached drawings. The figures show as follows:

FIG. 1: a schematic perspective view of a first embodiment of the substrate according to the invention;

FIGS. 2A, 2B and 2C: schematic illustrations of the phase transition of thermoresponsive microgels;

FIGS. 14 to 17: schematic illustrations of further embodiments of substrates according to the invention having density gradients of surface components; and FIG. 18: a schematic illustration of a substrate according to the invention having a cultivation cavity.

DETAILED DESCRIPTION OF PREFERRED EMBODIMENTS

Figure 3:
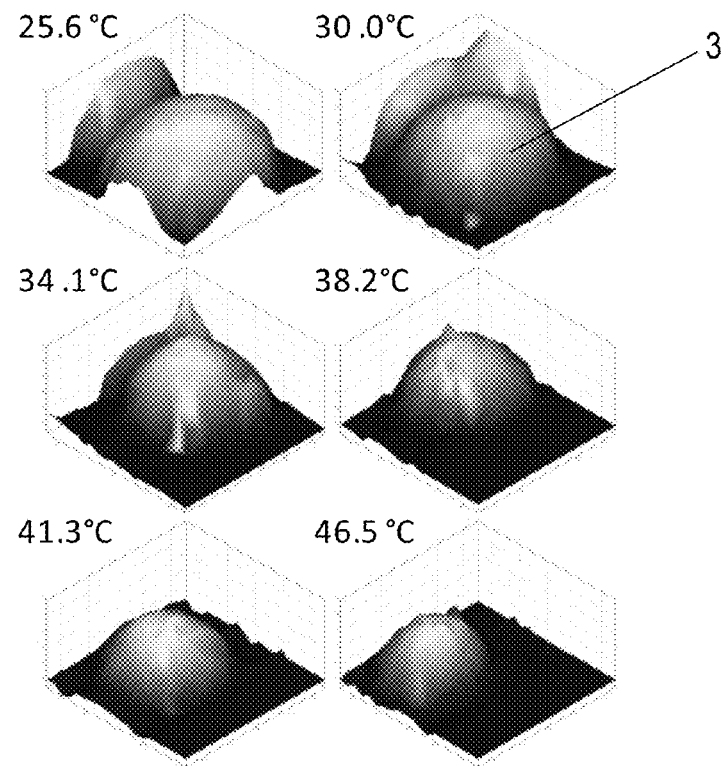
FIGS. 3A, 3B and 3C: experimental results showing the phase transition of thermoresponsive microgels.
Figure 3:
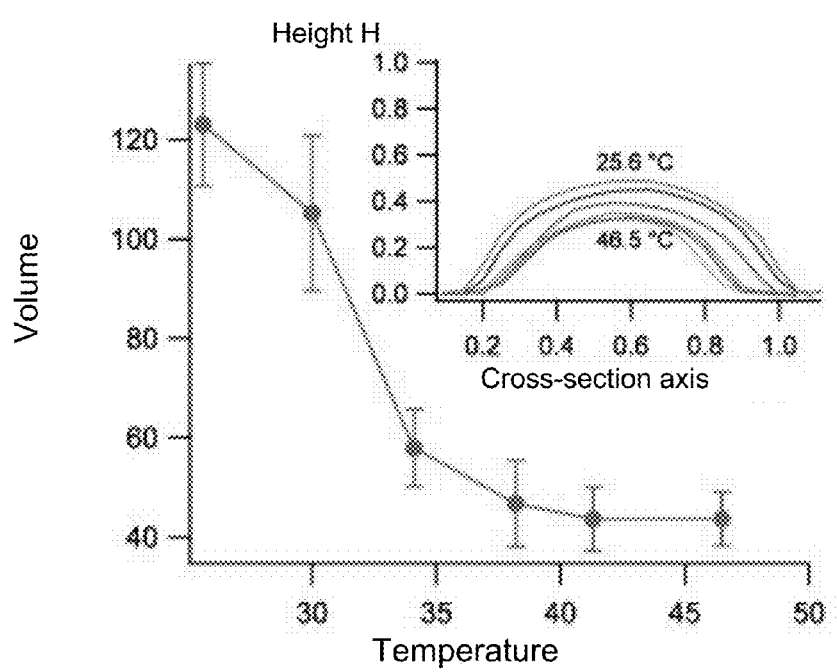
Figure 3:
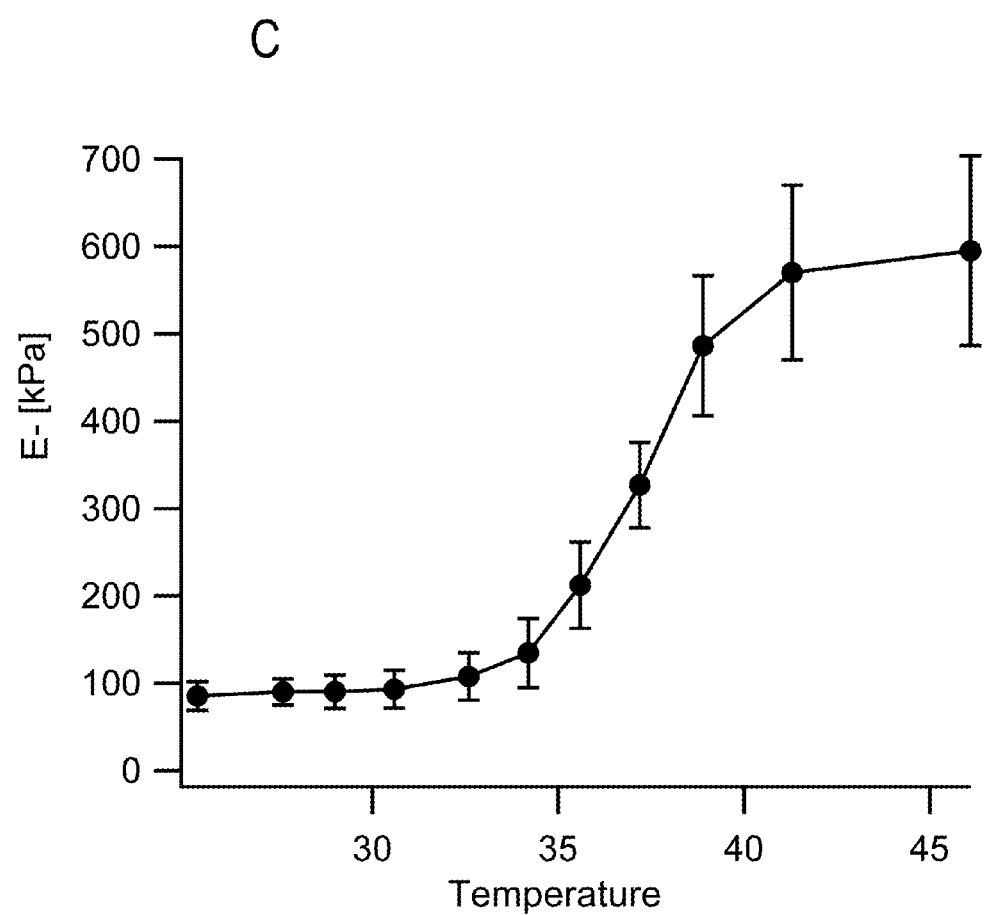

Preferred embodiments of the invention are described below with reference to the provision of thermoresponsive microgels on the carrier area of a cultivation substrate and its optionally provided functionalization. Details of cultivation methods, in particular methods for the handling of biological cells and their targeted influencing, are not described as they are known from the prior art. Furthermore, it is emphasized that the appended drawings are schematic, enlarged illustrations of sections of the cultivation substrate according to the invention. The implementation of the invention in practice is not limited to the illustrations, but possible with modified shapes, sizes and compositions of the substrates.

FIG. 1 shows—in a schematic perspective view—a first embodiment of the substrate 10 according to the invention having the substrate body 1, on the upper side (carrier area 2) of which the thermoresponsive microgels 3 are disposed. The substrate body 1 consists of e.g. metals, such as gold, titanium, platinum, glass, silicon wafer, or plastic, such as polystyrene, COP, polycarbonate, the surface of which forms the carrier area 2. The thermoresponsive microgels 3 are formed from the colloidal constituents of a thermoresponsive polymer. Other than the schematically illustrated spherical shape, the thermoresponsive microgels 3 can in practice have e.g. a hemispherical shape or a shape which is irregularly deformed depending on the coating conditions.

The thermoresponsive microgels 3 which are e.g. produced from PNIPam display the phase transition schematically illustrated in FIGS. 2A to 2C. The thermoresponsive microgels 3 comprise a cross-linked core 3.1 from which polymer chains 3.2 are formed radially protruding to the outside. Above a critical temperature ("Lower Critical Solution Temperature", LCST; switching temperature), which for cultivation applications is typically chosen to be a few ° C., e.g. 2° C. to 10° C. below 37° C., the polymer chains 3.2 are present in a collapsed state (FIG. 2A). When cooling down by a predetermined temperature difference $\Delta T$ and going below the critical temperature, the polymer chains 3.2 change into a non-collapsed (swollen) state (FIG. 2B). The size of the thermoresponsive microgels are described with a hydrodynamic radius which is lower in the collapsed state (R1) than in the non-collapsed state (R2). In the non-collapsed state, i.e. below the critical temperature, chain bridges 3.3 can remain between the polymer chains 3.2 (FIG. 2C) which is affecting the mechanical deformation properties and thus the adhesion properties of the substrate 10 for biological cells.

In a practical example, the radius R1 of the collapsed particles is chosen to be e.g. within the range of from 2 nm to 5 µm. Correspondingly, a radius R2 in the non-collapsed state can be achieved e.g. within the range of from 4 nm to 10 µm (e.g. 200 nm to 420 nm or 300 nm to 480 nm, see Wu et al. in "Coll. Poly. Sci." 272 (1994) 467; e.g. 92 nm to 200 nm, from 42 nm to 97 nm, from 29 nm to 65 nm and from 19 nm to 35 nm, see M. Andersson et al. in "J. Poly. Sci." B 44 (2006), 3305).

To immobilize the thermoresponsive microgels 3 on the carrier area 2, a microgel dispersion is initially produced which contains the microgel particles as colloidal particles. The radius R1 is set through the reaction conditions during the production of the microgel. The microgel dispersion can be stored stably.

In the production of the microgel dispersion, the following parameters of the particles are preferably set:
polymer chain length,
cross-linking density (e.g. formation of chain bridges),
particle radius R1 in the collapsed state,
particle radius R2 in the non-collapsed state,
Young's modulus in the collapsed state,
Young's modulus in the non-collapsed state, and
(optionally) radial stiffness gradient from the inside to the outside.

The microgel parameters are chosen depending on the application of the substrate 10. Although a complex parameter space is spanned with the mentioned properties, the choice of the parameters to be used concretely is possible depending on the cells to be cultivated and the cultivation conditions to be implemented (geometrically, physically and chemically), e.g. by simple tests or by using tabular values. The inventors have found that a strong correlation exists between the adhesion of biological cells on the thermoresponsive microgels 3 and their elastic properties such that it is possible to achieve an optimization of the cultivation conditions through the choice of elastic properties of the microgel in particular. For example, it was found that, when changing the Young's modulus of the microgels from 600 kPa (above the LCST) to 100 kPa (below the LCST) (see FIG. 3C), very good adhesion or cell detachment properties are obtained.

To prepare the substrate 10, the microgel is applied to the carrier area 2. A deposition technique known per se, such as e.g. spin coating, immersion, spraying, stamping or dispensing, e.g. with needles or dispenser nozzles, is used. The thermoresponsive microgels 3 which come into contact with the carrier area 2 form e.g. a covalent bond with the latter. The coated carrier area 2 is subsequently washed, e.g. with water to separate the excess, unbound particles. As schematically shown in FIG. 1, the thermoresponsive microgels 3 fixed to the carrier area 2 can form a regular, dense package or alternatively an irregular package with gaps.

Drying of the carrier area 2 provided with the microgels 3 can subsequently be scheduled. However, the drying process is not mandatory. Alternatively, an additional functionalization or the cultivation of biological cells can be scheduled immediately after the washing. Furthermore, sterilization of the exposed surface of the thermoresponsive particles, e.g. by ionizing radiation (gamma radiation) or gassing (e.g. with ethylene oxide) can be scheduled.

As schematically illustrated in FIG. 1, at least one biological cell 21 is adherently disposed on the surface with thermoresponsive microgels 3 in the collapsed state. By lowering the temperature, the phase transition of the thermoresponsive microgels 3 into the non-collapsed state can be induced in which the hardness of the surface with the thermoresponsive microgels 3 is reduced in comparison to the collapsed state. The at least one biological cell 21 has a reduced adhesion capability on the surface having the reduced hardness such that it can be detached, e.g. rinsed off by the liquid culture medium above the substrate (not shown in FIG. 1).

Experimental results showing the phase transition of thermoresponsive microgels 3 are shown exemplarily in FIG. 3. FIG. 3A illustrates the topography of individual microgels 3 (PNIPam) measured with an atomic force microscope for different temperatures. Swelling curves of the microgels 3 in the adsorbed state are shown in FIG. 3B. The small graphic in FIG. 3B shows mean height profiles in the apex of the microgels 3 (height H as a function of the diameter coordinate, each in µm). Finally, FIG. 3C illustrates the temperature dependence of the Young's modulus of the microgels derived from measurements with the atomic force microscope. While the Young's modulus is greater than 300 kPa at 37° C., the Young's modulus is reduced at 25° C. to values of less than 100 kPa. At the same time, the particles have a lower water content of about 65% at the higher temperature while the water content of the microgels is about 90% at 25° C.

The experimental results show that the thermal response behavior of the microgels 3, in particular the sharp temperature profile of the phase transition in the adsorbed state is comparable with the liquid state. Experimental tests with mouse fibroblasts have shown that the adhesion of the fibroblasts on the surface within the temperature range in which the phase transition was measured via the change in the Young's modulus could be altered from an adherent state at temperatures above the phase transition into a non-adherent state at temperatures below the phase transition.

Above the phase transition, e.g. at 37° C., the cells have a bigger contact area with the substrate than at temperatures below the phase transition.

Figure 4:
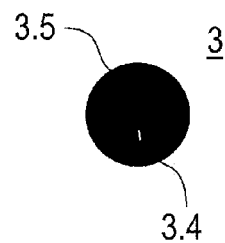
FIG. 4: a schematic illustration of a thermoresponsive microgel having a core-shell structure.
Figure 5:
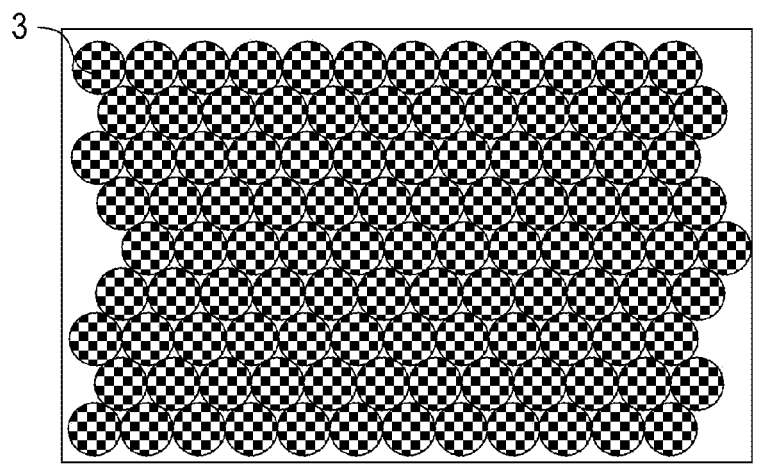
FIGS. 5, 6, 7, 8A and 8B: further embodiments of substrates according to the invention.
Figure 6:
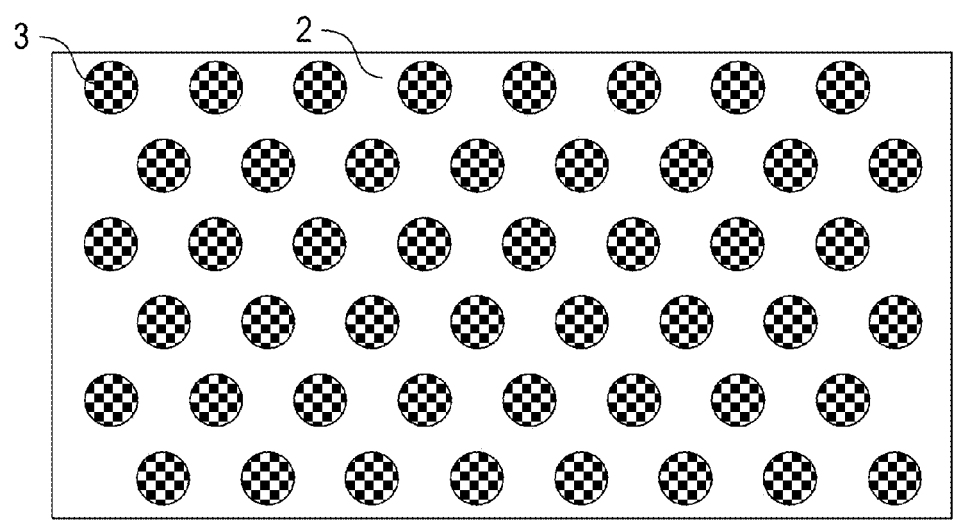

FIGS. 4 to 6 show variants of the invention which can be chosen in particular depending on the concrete cultivation task. For example, according to FIG. 4, a thermoresponsive microgel 3 having a core-shell structure is provided. The core 3.4, e.g made of latex, is unchangeable under the cultivation conditions and in particular in the case of a temperature change. The shell 3.5 is formed by the thermoresponsive polymer, e.g. PNIPam. The preparation of a microgel dispersion for the formation of particles having a core-shell structure is known per se (see Hellweg et al. in "Langmuir" 20 (2004), 4330; Fernandez-Barbero et al. in "Phys Rev E 66" (2002), 051803/1-10). The fixing of thermoresponsive microgels 3 having a core-shell structure on the carrier area and the further treatment of the substrate are performed as described above with regard to FIG. 1.

The thermoresponsive microgels 3 can form a closed (FIG. 5) or an non-closed monolayer interrupted by gaps (FIG. 6) on the carrier area 2. The regular array of the thermoresponsive microgels according to FIG. 5 can be generated by self-organization (formation of the densest package). In contrast, with the non-closed layer according to FIG. 6, the regular array of the thermoresponsive microgels 3 can be achieved by a pretreatment of the carrier area, e.g. with locally applied adhesion-promoter islands. Differing from FIGS. 5 and 6, the thermoresponsive microgels 3 can form irregular arrays on the carrier area 2.

Figure 7:
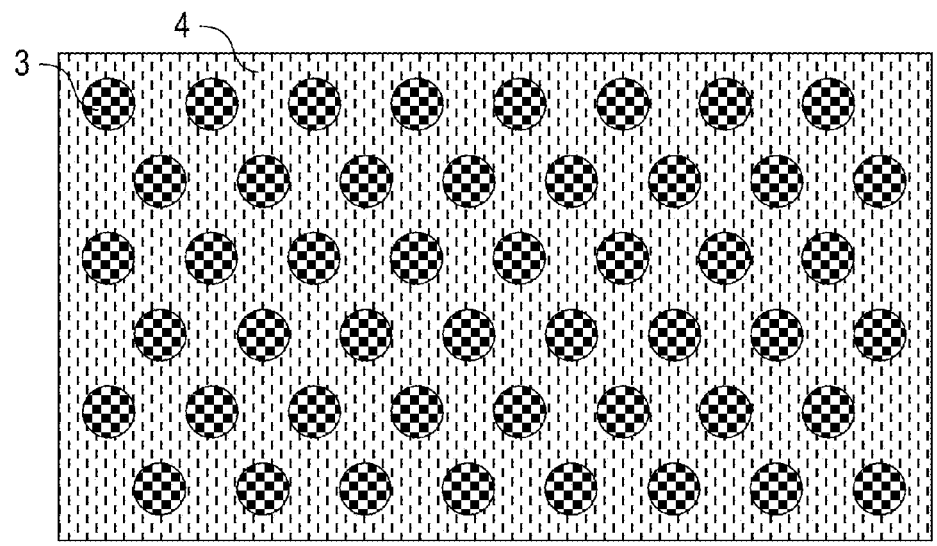
Figure 8:
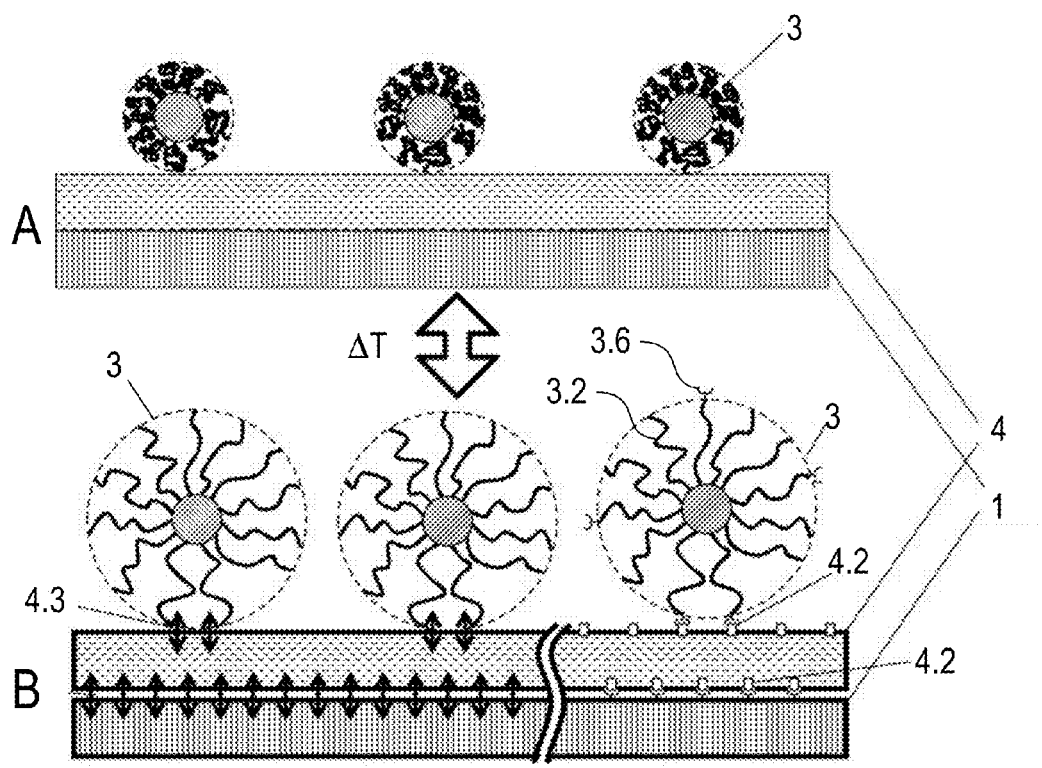

FIGS. 7 and 8 schematically illustrate that the anchoring of the thermoresponsive microgels 3 on the carrier area 2 can be improved if an adhesion promoter 4 is disposed on the latter. The adhesion promoter 4 can cover the carrier area 2 completely (FIG. 7) and thus form the modified carrier area, which is exposed for the fixing of the thermoresponsive microgels 3. FIG. 8 shows a section of the substrate 10 according to the invention with the thermoresponsive microgels 3 in the collapsed state (FIG. 8A) above the critical temperature and in the non-collapsed state (FIG. 8B) below the critical temperature. Furthermore, FIG. 8B schematically illustrates the binding variants provided between the adhesion promoter 4 with the substrate body 1 on one hand and the thermoresponsive particles 3 on the other hand. For example, binding sites 3.6 can be provided at the free ends of the polymer chains 3.2 of the thermoresponsive microgels 3 for a covalent or biospecific binding 4.1 with the adhesion promoter 4. The binding sites 3.6 can be formed during the production of the microgel. The covalent bonds are based on e.g. epoxy, carboxy, amino, hydrazide, thiol or maleimide bonds at the ends of the polymer chains 3.2. To form the covalent or biospecific bond 4.1, the adhesion promoter layer 4 is correspondingly provided with binding sites 4.2 which react with the binding sites 3.6 of the thermoresponsive microgels 3. At the same time, the binding sites 4.2 form covalent or biospecific bonds with the substrate body 1. In particular, the biospecific bonds can be formed by receptor-ligand bonds, such as e.g. between streptavidin and biotin.

In the left part of FIG. 8B, it is schematically illustrated that the effect of the adhesion promoter 4 can be based on an unspecific interaction 4.3 with the thermoresponsive particles 3 on the one hand and with the substrate body 1 on the other hand.

The adhesion promoter 4 comprises e.g. a biotin layer having a thickness of from 1 nm to 1 μm (see Spinke et al. in "J. Chem. Phys." 99 (1993), 7012; Hong et al. in "Progr. Colloid Polym. Sci." 93 (1993), 98; Zao et al. in "Electroanal." 18 (2006), 1737). The layer is formed on the surface of the substrate body 1 with methods known per se, such as e.g. spin coating or self-assembling from the solution.

Figure 9:
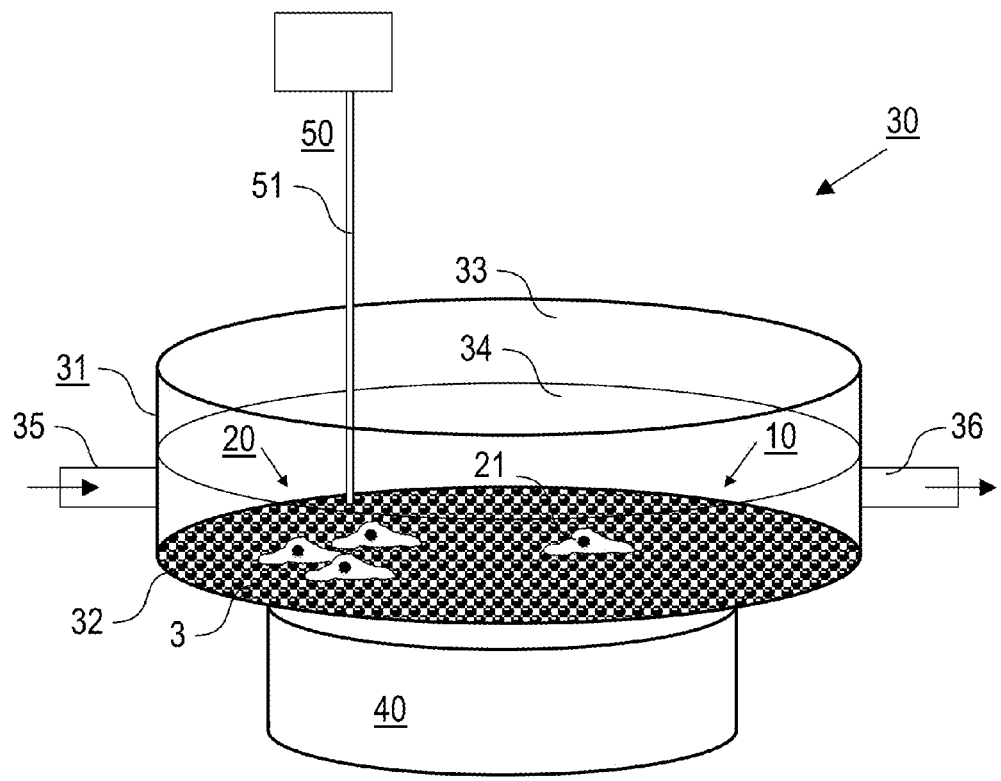
FIG. 9: a schematic illustration of a cultivation device equipped with the substrate according to the invention.

The substrate 10 according to the invention can be part of a cultivation device 30, as illustrated exemplarily in FIG. 9. The cultivation device 30 comprises a culture vessel 31 having a bottom 32 and a circumferential side wall 33. The culture vessel 31 is intended for receiving a liquid culture medium 34 which can be introduced into the culture vessel 31 via a supply line 35 and can be removed from the culture vessel 31 via an outlet line 36. The substrate 10 according to the invention is arranged on the bottom 32. Alternatively, the bottom 32 forms the substrate 10. The thermoresponsive particles 3 are disposed in an exposed manner on the side of the substrate 10 facing the inside of the culture vessel 31. Biological cells 20, 21 are present on the substrate 10.

Furthermore, FIG. 9 schematically illustrates a device for setting the temperature 40 and a manipulator device 50. By means of the device for setting the temperature 40, the temperature of the substrate 10 or of subregions (segments) of the substrate 10 can be set in a targeted manner from a temperature above the critical temperature of the phase transition of the thermoresponsive microgels 3 to a temperature below said critical temperature. The device for setting the temperature comprises e.g. a heating device, such as e.g. a resistance heater, or a combination of a heating device and a cooling device, such as e.g. a Peltier cooler. The manipulator device 50 comprises e.g. a supply line 51 through which a cell suspension can be rinsed into the culture vessel 31.

Furthermore, the cultivation device 30 can be equipped with a monitoring device, e.g. a microscope, and a measuring device, e.g. a temperature sensor (not depicted).

Figure 11:
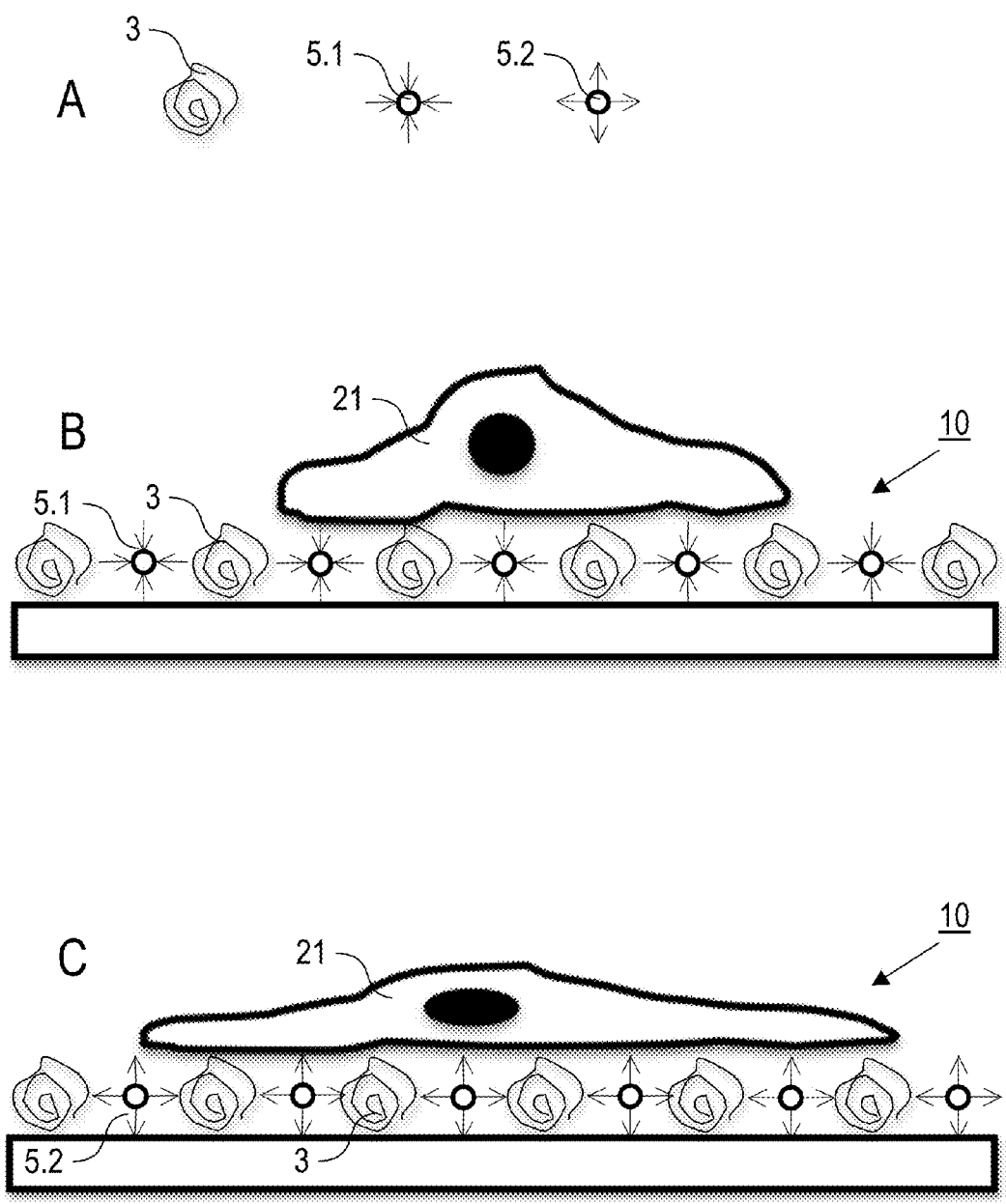
Figure 12:
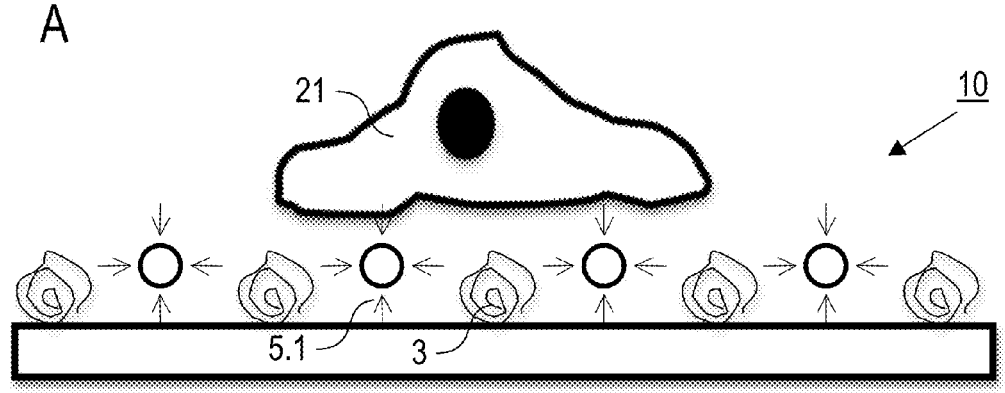
Figure 12:
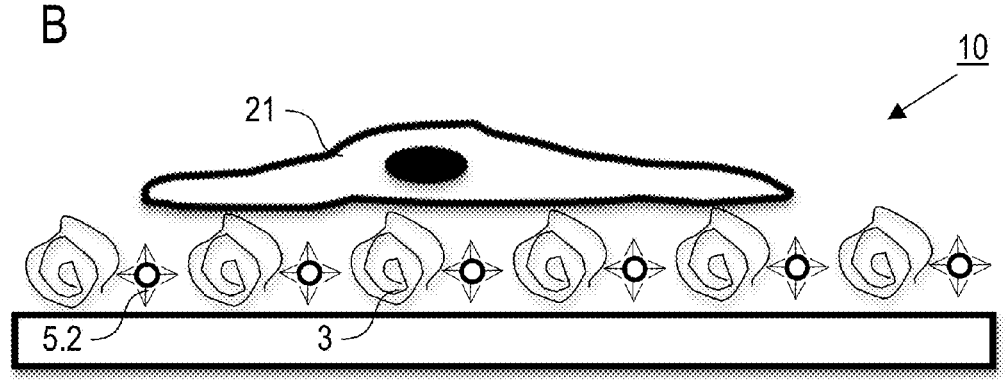
Figure 13:
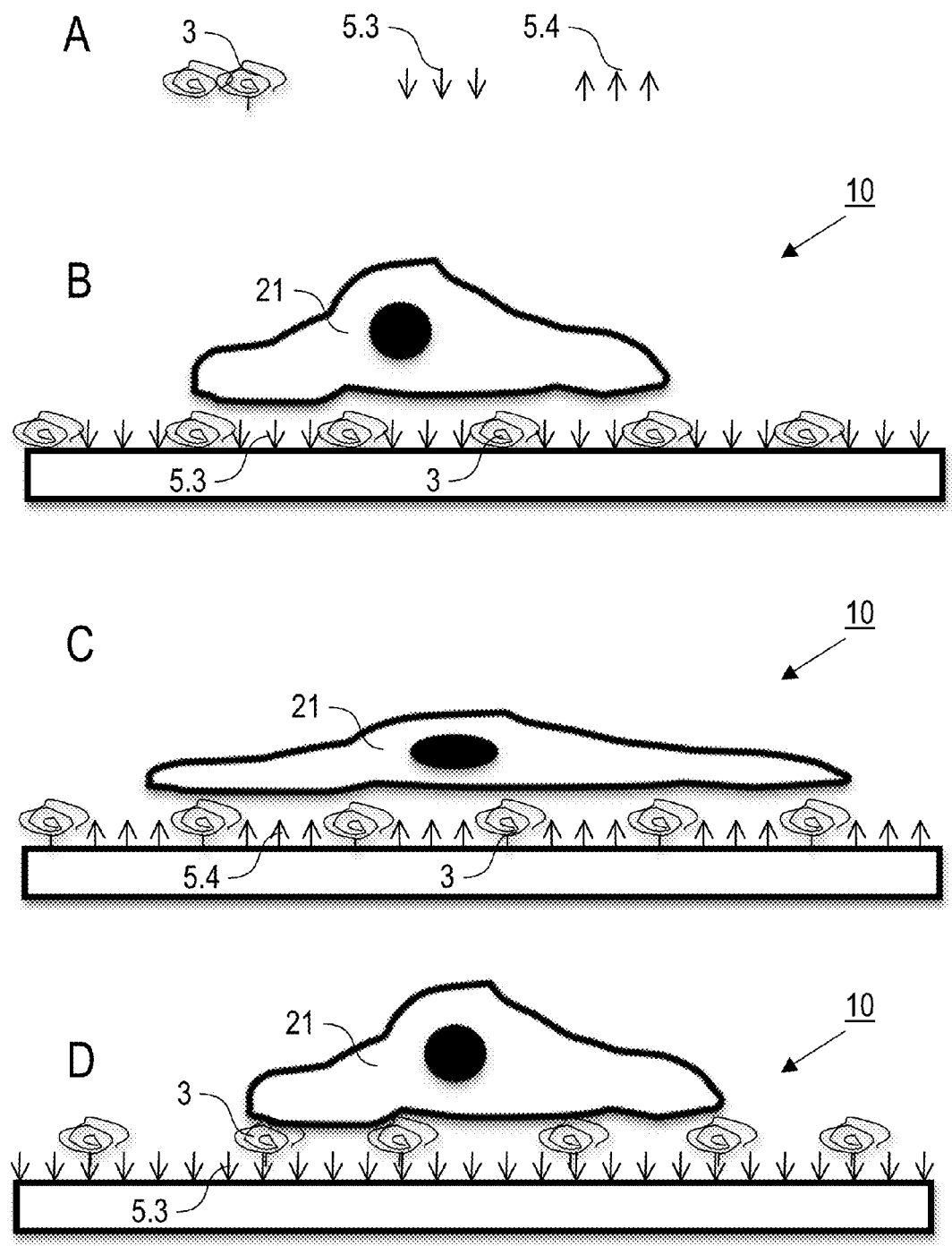
Figure 14:
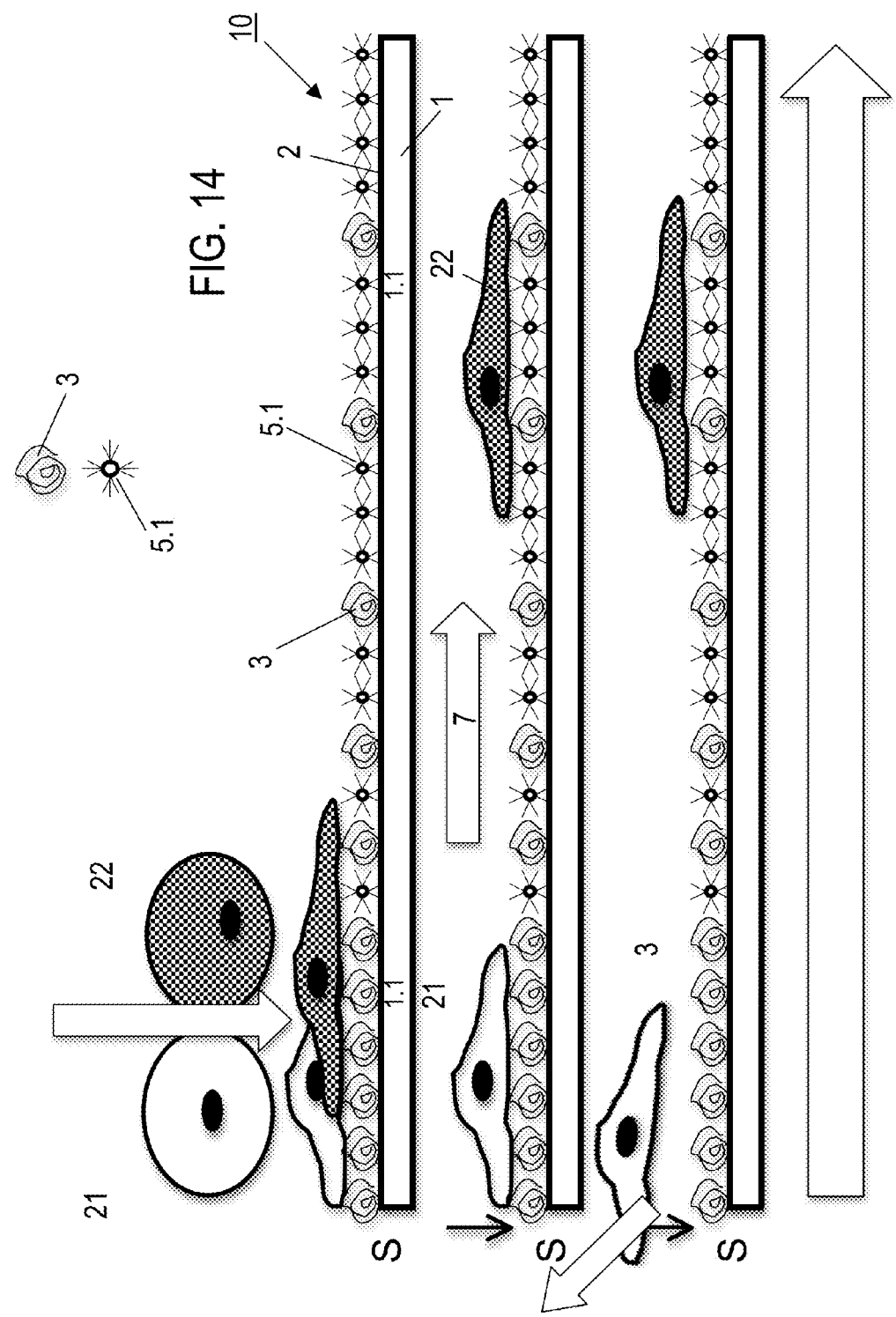
Figure 15:
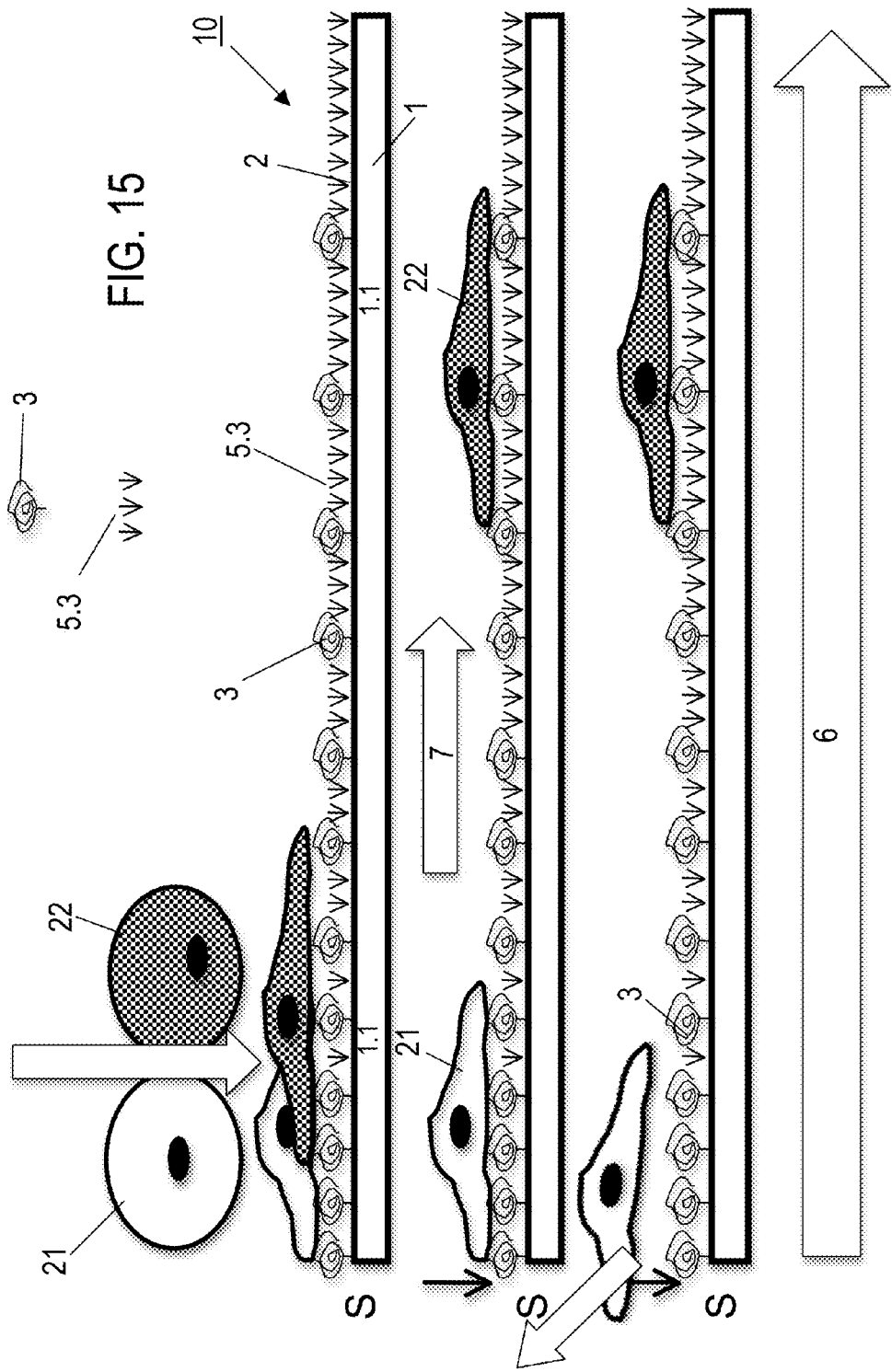

FIGS. 10 to 17 illustrate different variants of the functionalization of a substrate according to the invention with at least one modulator substance which can be provided on the carrier area of the substrate with modulator particles (e.g. FIGS. 10 to 12) and/or as a modulator layer (e.g. FIGS. 13, 15). The at least one modulator substance generally comprises a single chemical substance or a composition of chemical substances to which the biological cells have a changed adhesion capability in comparison to the thermoresponsive microgels (see above for examples) and/or with which cellular reactions are inducible in the biological cells.

Substances triggering cellular reactions are generally substances which cause e.g. an increased adhesion, a migration (cell migration), a differentiation (in particular stem cell differentiation), a change of the activation status or a change of the malignity by binding to surface receptors of the biological cells. Such substances are e.g.:

chemokines, such as e.g. FGF induce chemotaxis, or osteonectin (induces differentiation of stem cells into cardiac muscle cells).

The combination of differently acting modulator substances advantageously allows for the targeted setting of predetermined physical or chemical surface properties. As the at least one modulator substance can be added to the dispersion of colloidal particles of the thermoresponsive polymer during the preparation of the microgel, the thermoresponsive microgels and the at least one modulator substance can be freely combined like modules. The surface of the substrate according to the invention can be designed like a modular building block system.

Figure 10:
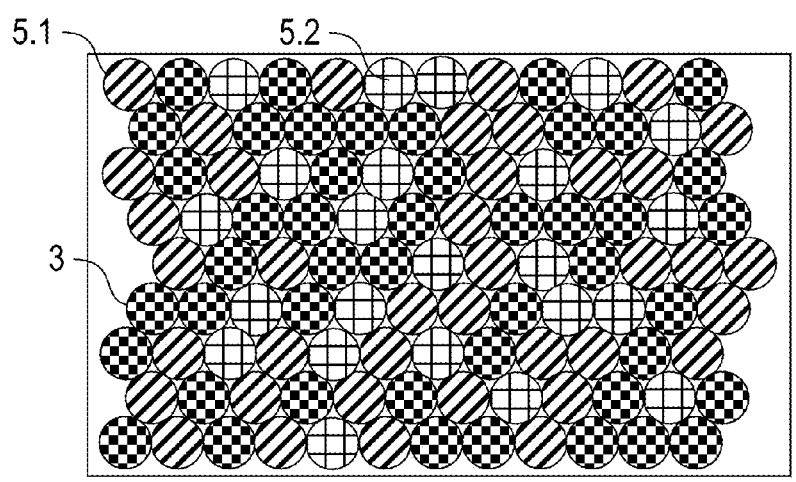
FIGS. 10, 11A, 11B, 11C, 12A, 12B, 13A, 13B, 13C and 13D: schematic illustrations of further embodiments of substrates according to the invention equipped with at least one modulator substance.

In the example schematically shown in FIG. 10, thermoresponsive microgels 3, plastic particles coated with cell-attracting molecules (adhesion-increasing modulator particles 5.1) and plastic particles coated with cell-repelling molecules (adhesion-reducing modulator particles 5.2) are combined. The modulator particles 5.1, 5.2 have a diameter which is chosen e.g. within the range of from 50 nm to 1 µm.

FIG. 11 schematically illustrates the different effects of the combination of thermoresponsive microgels 3 with adhesion-increasing modulator particles 5.1 and adhesion-reducing modulator particles 5.2 (symbolized in FIG. 11A). According to FIG. 11B, the adhesion-increasing modulator particles 5.1 cause through a relatively high number of binding sites for the adherent attachment of the cell 21 that a relatively small contact area is formed between the cell 21 and the substrate surface. With the smaller contact area, the cell 21 contacts a relatively small number of thermoresponsive microgels 3 such that their effect is reduced in a temperature-dependent phase transition. As a result, a strong bond of the cell 21 to the substrate 10 is achieved.

According to FIG. 11C, adhesion-reducing modulator particles 5.2 cause the opposite effect. The cell 21 is distributed on the surface of the substrate 10 to find binding sites for the adhesion contacts of the cell 21. The cell 21 correspondingly gets into contact with a relatively large number of thermoresponsive microgels 3. A phase transition of the thermoresponsive microgels 3 thus has a stronger effect than in the case of the adhesion-increasing modulator particles 5.1 (FIG. 11B). The adhesion of the cell 21 on the surface of the substrate 10 is reduced.

By setting the quantitative mixing ratios of the thermoresponsive microgels 3 with at least one type of the modulator particles 5.1, 5.2 in the dispersion for the preparation of the microgels, the adhesion properties (adherence or detachment parameters) of the substrate surface can thus advantageously be varied across a wide range while the thermoresponsive character of the surface is maintained and the surface possesses optimal adhesion properties for one cell type or several cell types. Advantageously, the mixing ratios in the carrier solutions for the preparation of the dispersions can be generated simply by weighing. The use of the microgel dispersion containing the particles of the thermoresponsive polymer and the modulator particles allows for the concerted transfer onto the carrier area of the substrate in a single deposition step.

The size ratios of the biological cell 21 on the one hand and the microgels 3, 5.1 and 5.2 chosen in the schematic illustration of FIG. 11 are chosen for practical reasons in terms of the drawing. In contrast to the illustration, significantly smaller particle sizes, e.g. up to 50 nm or less, or else bigger particles, e.g. 10 µm, can be used.

According to another variant of the invention, particles having different sizes can be combined on the surface of the substrate 10, as exemplarily illustrated in FIG. 12. For example, the adhesion-increasing modulator particles 5.1 can have a bigger radius than the thermoresponsive microgels 3 (FIG. 12A). In this case, the adhesion-increasing effect of the modulator particles 5.1 is enhanced as these are better accessible for the cell 21 in comparison to the thermoresponsive microgels 3. In contrast thereto, according to FIG. 12B, the effect of the modulator particles 5.2 is reduced with adhesion-reducing modulator particles 5.2 whose radius is smaller than the radius of the thermoresponsive microgels 3. Further combinations, such as e.g. smaller adhesion-increasing modulator particles 5.1 and/or bigger adhesion-reducing modulator particles 5.2, are likewise possible.

As a result, not only the adhesion properties of the surface can be set but it is also possible to provide a certain granularity of the surface. The provision of a grainy surface means that a surface topology with elevations and indentations is generated. The granularity of the surface can advantageously be adapted to typical dimensions of the adhesion pattern of a certain cell type (human and bovine capillary endothelial cells, see C. S. Chen et al. in "Science" 276 (1997), 1425; and C2C12 muscle cells, see U. Joos et al. in "Eur. J. Cell Bio." 85 (2006), 225).

FIG. 13 illustrates another variant of the invention in which the at least one modulator substance in combination with the thermoresponsive microgels 3 is provided as an adhesion-increasing modulator layer 5.3 or as an adhesion-reducing modulator layer 5.4 (FIG. 13A). In this case, too, a modular design of the surface of the substrate 10 is advantageously achieved by superposing the interaction of the cell 21 with the different components. In contrast to the use of modulator particles, the at least one modulator substance is not added to the microgel but provided in an additional deposition step by coating the carrier area of the substrate body before or after the application of the thermoresponsive microgels.

FIG. 13B illustrates the effect of an adhesion-increasing modulator layer 5.3 which analogously to FIG. 11B results in a reduced contact area of the cell 21 and thus a reduced effect of the thermoresponsive microgels 3. In contrast thereto, according to FIG. 13C, the adhesion-reducing modulator layer 5.4 provides for a distribution of the cell and thus an enhanced effect of the thermoresponsive microgels 3.

While the thermoresponsive microgels 3 are coupled in the variants of FIGS. 13B and 13C via one of the above-described connection types with the substrate body, according to FIG. 13D, the alternative possibility exists to connect the thermoresponsive microgels 3 with the adhesion-increasing modulator layer 5.3. In this case, the adhesion-increasing modulator layer 5.3 fulfills a double function as an adhesion promoter (see above, FIGS. 7, 8) and as a modulator substance.

According to another (not depicted) variant, the thermoresponsive microgels 3 can initially be connected with the substrate body 1 and the adhesion-increasing or adhesion-reducing modulator layer can subsequently be applied.

Figure 16:
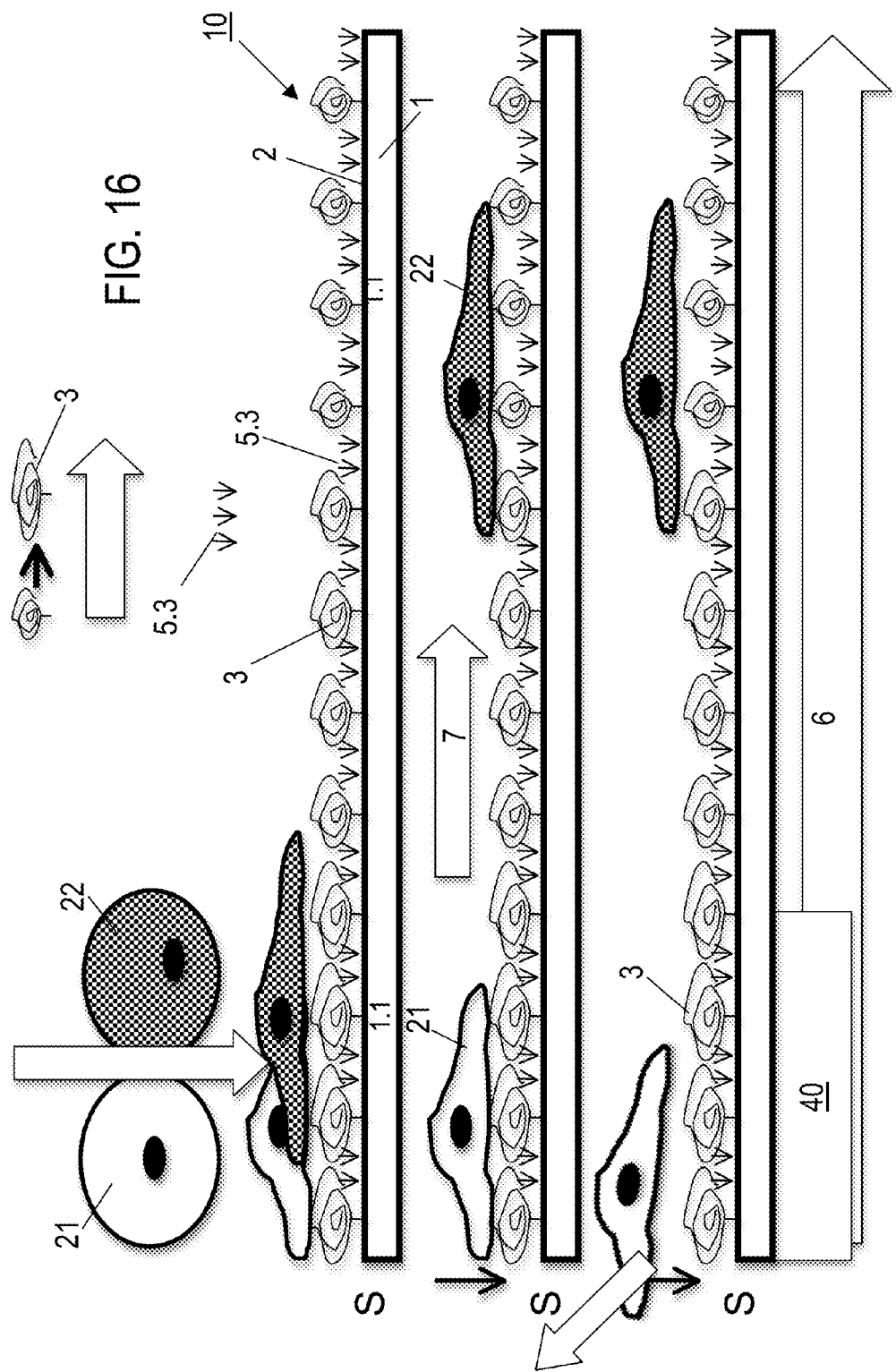

FIGS. 14, 15 and 16 illustrate embodiments of the invention in which the thermoresponsive microgels, the adhesion promoter and/or the modulator substance are disposed on the carrier area of the substrate body with at least one density gradient. These embodiments are particularly beneficial for the manipulation of biological cells in the cultivation in co-cultures. By means of the formation of density gradients, the surface properties of the substrate can be modified in such a way that a migration (cell migration) of the adherent cells depending on the cell type is induced. To this end, a concentration gradient (FIGS. 14, 15) and/or a function gradient (FIG. 16) of at least one modulator substance having chemotactic properties can be provided.

According to FIG. 14, thermoresponsive microgels 3 and adhesion-increasing modulator particles 5.1 are disposed on the carrier area 2 of the substrate body 1 in such a way that a higher area density of the thermoresponsive particles 3 is generated in a first subregion 1.1 in comparison to the adhesion-increasing modulator particles 5.1 and, vice versa, a lower density of the thermoresponsive microgels 3 is generated in a second subregion 1.2 in comparison to the adhesion-increasing modulator particles 5.1. As a result, a density gradient 6 is formed which is characterized along the carrier area 2 by an increasing area density of the adhesion-increasing modulator particles 5.1 or a decreasing area density of the thermoresponsive microgels 3. The density gradient 6 schematically illustrated in FIG. 14 can in practice be generated stepwise by the deposition of microgels having different compositions on different subregions of the substrate body 1.

According to FIG. 14, to cultivate biological cells 21 from a first cell type of interest together with feeder cells 22, the formation of the co-culture is provided in the first subregion 1.1 with a high content of the thermoresponsive particles 3 (step S1). Following the cultivation comprising e.g. a differentiation of the cells 21, the feeder cells 22 migrate out of the first subregion 1.1 under the specific action of the adhesion-increasing modulator particles 5.1 (migration 7, step S2). Subsequently, the detachment of the cells of interest 21 takes place by inducing the phase transition of the thermoresponsive microgels 3 by a temperature change of the substrate 10 and significantly reducing the adhesion capability for biological cells 21 in the subregion 1.1. The cells 21 can then be removed from the substrate 10, e.g. with a manipulation device, as shown in FIG. 9.

To instigate the cells to migrate in a cell type-specific manner, a number of modulator substances is available. For example, fMLP (formyl-methionyl-leucyl-proline) only affects the migration of HL 60 leukemia cells while other cell types remain unaffected.

The principle of the selective migration 7 of one cell type from a mixture of adherent cells schematically shown in FIG. 14 can correspondingly be generalized to the mixture of more than two cell types, wherein the adhesion-increasing modulator substance is chosen such that at least one cell type from the mixture migrates away or at least one cell type remains unchanged and shows no migration. Through this, small cell samples having low cell numbers, in particular of less than $10^5$ cells, can advantageously be separated after the co-cultivation.

The separation of mixtures of different cell types is not limited to the use of adhesion-increasing modulator particles. Alternatively or additionally, thermoresponsive particles 3 can be combined with adhesion-increasing modulator layers 5.3, as schematically illustrated in FIG. 15. A density gradient 6 is formed between a first subregion 1.1 of the substrate body 1 with an increased area density of the thermoresponsive microgels 3 and another subregion 1.2 of the substrate body 1 with an increased area density of the adhesion-increasing modulator layer 5.3. Analogous to FIG. 14, the deposition and co-culture of the biological cells of interest 21 together with the feeder cells 22 is initially performed (step S1), subsequently the cell type-specific migration 7 of the feeder cells 22 out of the cell mixture (step S2) and finally the detachment of the cell of interest 21 via the temperature-induced phase transition of the thermoresponsive microgels 3 (step S3).

Different options are available for the detachment of the cells 21. According to FIGS. 15 and 16, the temperature of the entire substrate 10 can be lowered below the critical temperature (LCST). This is in particular possible if the cells 22 remaining adherent in the subregion 1.2 remain unaffected by the phase transition of the thermoresponsive particles 3. Alternatively, a local reduction of the temperature can be provided, as schematically illustrated in FIG. 16. In this embodiment of the invention, the device for setting the temperature 40 (see also FIG. 9) is operatively arranged locally on the subregion 1.1 of the substrate body 1. In this case, the phase transition of the thermoresponsive microgels 3 can be induced locally limited within the subregion 1.1 while the thermoresponsive microgels remain unchanged in other subregions.

However, the cell type-specific migration on the substrate surface does not necessarily require a density gradient. Alternatively or additionally, chemotactically acting substances 8 can be added to the culture medium, as schematically illustrated in FIG. 17.

According to FIG. 17, a substrate 10 according to the invention is used, on whose substrate body 1 the thermoresponsive particles 3 are disposed homogeneously distributed. Following the co-cultivation of the cells 21, 22 on the substrate 10 (step S1), the addition of chemotactically acting substances 8 to the culture medium is performed such that a migration 7 of the cells is induced. By choosing the chemotactically acting substance 8, the migration 7 can be induced in a cell type-specific manner.

For example, fMLP only causes a migration of HL 60 leukemia cells while cells from cell lines obtained from healthy tissue remain unaffected.

To detach the cells of interest 21, a locally limited temperature reduction takes place in step S3. The thermoresponsive particles 3 show the phase transition in the non-collapsed state such that the cell 21 can be detached.

FIG. 18 shows another variant of the invention in which the substrate 10 is equipped with a cultivation cavity 9. The cultivation cavity 9 can be used for the in vitro simulation of differentiation processes in stem cell niches. For example, in the biological organism, stem cells are held available in cavities with a predetermined biochemical and/or cellular lining (see David T. Scadden in "Nature" 441 (2006), 1075; M. C. Dusseiller et al. in "Biointerphases" 1 (2006), P1) and subjected to a differentiation. An example for such a stem cell niche are hair follicles.

By means of the cultivation cavity 9 of the substrate 10 according to the invention, a micro-environment for biological cells 21 is created in which the conditions in the organism are reproduced. Conventional cell manipulation techniques for the lining of artificial cultivation cavities with biological cells require the use of optical tweezers or dielectrophoretically acting elements. This is disadvantageous in terms of the apparatus expenditure and the complex methods. This problem is solved with the substrate according to the invention according to FIG. 18 by the fact that cells targetedly migrate into the cultivation cavity 9.

According to step S1 in FIG. 18, a cell mixture of biological cells 21, 22 which are to be disposed in the cultivation cavity 9 are applied in a first subregion 1.1 of the substrate body 1 and optionally cultivated. In a second step S2, the targeted migration of the cells 21, 22 into the cultivation cavity 9 takes place wherein one of the above-mentioned mechanisms, e.g. a density gradient, and/or a chemotactic substance acting from the culture medium are used.

The features of the invention disclosed in the previous description, the drawings and the claims can be significant individually as well as in combination for the realization of the invention in its different embodiments.

The invention claimed is:

1. A substrate for receiving biological cells, comprising:
a substrate body having a carrier area,
thermoresponsive microgel particles fixed on the carrier area, and
modulator particles fixed on the carrier area and comprising at least one modulator substance with which biological cells have an adhesion capability which differs from the adhesion capability of the biological cells to the thermoresponsive microgel particles, and/or with which cellular reactions are inducible by binding to surface receptors of the biological cells,
wherein the thermoresponsive microgel particles: (a) consist of at least one thermoresponsive polymer and/or (b) have a core-shell structure with shells consisting of at least one thermoresponsive polymer, and
wherein the at least one modulator substance of the modulator particles is effective to influence cultivation conditions on the substrate without affecting a temperature behavior of the thermoresponsive microgel particles.

2. The substrate according to claim 1, in which the thermoresponsive microgel particles comprise at least one uncharged and non-ionizable polymer.

3. The substrate according to claim 1, in which the thermoresponsive polymer microgel particles comprise at least one polymer that is a homopolymer of one of the following formulas or a copolymer of more than one of the following formulas:

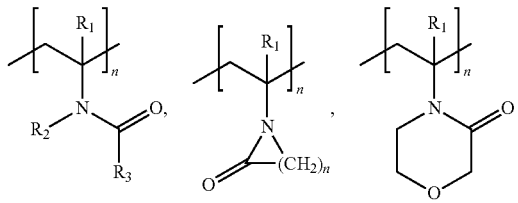

with $R_1$=H or alkyl, with $R_2$ and $R_3$=H, alkyl, alkenyl, alkynyl or aryl, with $2 \leq n \leq 10$.

4. The substrate according to claim 1, in which at least one terminal unit of a backbone of the polymer includes a coupling group to the carrier area.

5. The substrate according to claim 1, in which the thermoresponsive microgel particles comprise:
poly-(N-isopropyl acrylamide).

6. The substrate according to claim 1, in which the thermoresponsive microgel particles comprise at least two different polymers and/or have different diameters.

7. The substrate according to claim 1, in which
the thermoresponsive microgel particles have a diameter which is at least 10 nm and at most 50 μm.

8. The substrate according to claim 1, in which
the thermoresponsive microgel particles have core-shell structures.

9. The substrate according to claim 8, having at least one of the following features:
only the shells of the thermoresponsive microgel particles are thermoresponsive,
cohesion of the cores of the thermoresponsive microgel particles is caused by secondary-valence interactions,
cohesion of the cores of the thermoresponsive microgel particles is caused by chemical cross-linking,
a thickness of the shells of the thermoresponsive microgel particles is at least 10 nm,
and/or one of the following features:
polymer chains in the shells of the thermoresponsive microgel particles are not cross-linked, or
polymer chains in the shells of the thermoresponsive microgel particles are cross-linked, wherein the number of cross-linking points between the chains is no greater than 1 per 20 repeating units compared to repeating units of chains that are not cross-linked.

10. The substrate according to claim 1, in which the thermoresponsive microgel particles comprise a monolayer.

11. The substrate according to claim 1, in which
the carrier area further comprises an adhesion promotor which is not the at least one modulator substance of the modulator particles.

12. The substrate according to claim 1, further comprising a density gradient on the carrier area, wherein the density gradient comprises at least one of a thermoresponsive microgel particles density gradient, an adhesion promoter density gradient and a modulator substance particles density gradient.

13. The substrate according to claim 1, further comprising at least one cultivation cavity on the carrier area.

14. The substrate according to claim 1, in which the substrate body is part of a cultivation device.

15. A method for the preparation of a substrate according to claim 1, comprising the steps:
providing a substrate body having a carrier area,
preparing a dispersion of thermoresponsive microgel particles,
contacting the dispersion of the thermoresponsive microgel particles with the carrier area,
fixing the dispersion of the thermoresponsive microgel particles on the carrier area, and
contacting modulator substance particles with the carrier area.

16. The method according to claim 15, further comprising the step of:
applying an adhesion promoter to the carrier area, and
sterilizing the carrier area.

17. A method for cultivating biological cells on the substrate according to claim 1 comprising the steps:
contacting biological cells with the substrate, and
cultivating the biological cells under incubation conditions to cause adherence, growth, differentiation and/or migration of the biological cells.

18. The method according to claim 17, wherein:
the adherence of the biological cells on the substrate is effected by adjusting the temperature of the incubation conditions,
the migration of at least one type of the biological cells is effected by the presence of a density gradient of modulator substance particles that specifically act on the at least one type of the biological cells, and/or
the migration of at least one type of the biological cells is effected by the presence of a density gradient of modulator substance particles on the substrate such that the biological cells migrate into a cultivation cavity on the carrier.

19. A substrate for receiving biological cells, comprising:
a substrate body having a carrier area,
thermoresponsive microgel particles fixed on the carrier area, and modulator particles fixed on the carrier area and comprising at least one modulator substance with which biological cells have an adhesion capability which differs from the adhesion capability of the biological cells to the thermoresponsive microgel particles, and/or with which cellular reactions are inducible by binding to surface receptors of the biological cells, wherein the thermoresponsive microgel particles are spaced apart from the modulator particles such that the at least one modulator substance of the modulator particles is effective to influence cultivation conditions on the substrate without affecting a temperature behavior of the termoresponsive microgel particles.

* * * * *